US006332089B1

(12) United States Patent
Acker et al.

(10) Patent No.: US 6,332,089 B1
(45) Date of Patent: Dec. 18, 2001

(54) MEDICAL PROCEDURES AND APPARATUS USING INTRABODY PROBES

(75) Inventors: David E. Acker, Setauket, NY (US); Assaf Govari, Kiryat Haim; Maier Fenster, Petach Tikva, both of (IL); Avishai Shapiro, Setauket, NY (US)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/117,803

(22) PCT Filed: Feb. 14, 1997

(86) PCT No.: PCT/US97/02335

§ 371 Date: Sep. 18, 1998

§ 102(e) Date: Sep. 18, 1998

(87) PCT Pub. No.: WO98/29709

PCT Pub. Date: Aug. 21, 1997

Related U.S. Application Data

(60) Provisional application No. 60/011,721, filed on Feb. 15, 1996, provisional application No. 60/012,275, filed on Feb. 26, 1996, and provisional application No. 60/031,824, filed on Nov. 26, 1996.

(30) Foreign Application Priority Data

Aug. 26, 1996 (IL) .......................................... 119137
Sep. 17, 1996 (IL) .......................................... 119262

(51) Int. Cl.$^7$ .................................................. A61B 5/00
(52) U.S. Cl. ............................................ 600/424; 128/899
(58) Field of Search ................................... 600/300, 424; 606/158; 128/898, 899

(56) References Cited

U.S. PATENT DOCUMENTS 3,644,825  2/1972  Davis, Jr. et al. ..................... 324/41
3,868,565  2/1975  Kuipers ............................... 324/34 R
4,017,858  4/1977  Kuipers ............................. 343/100 R (List continued on next page.)

FOREIGN PATENT DOCUMENTS

| 0 246 176 | 11/1987 | (EP) . |
| WO 94/00050 | 1/1994 | (WO) . |
| WO 94/04938 | 3/1994 | (WO) . |
| WO 94/06349 | 3/1994 | (WO) . |
| WO 94/23647 | 10/1994 | (WO) . |
| WO 94/28782 | 12/1994 | (WO) . |

(List continued on next page.)

OTHER PUBLICATIONS

"Effects of laser irradiation delivered by flexible fiberoptic system on the left ventricular internal myocardium" American Heart Journal, Sep. 1983, pp. 587–590.

Dorothy Bonn, "High–Power laser help the Ischaemic Heart", The Lancet, vol. 348 (Jul. 13, 1996) p. 118.

Mahmood Mirhoseini et al. "Transmyocardial Laser Revascularization: A Review" Journal of Clinical Laser Medicine & Surgery. vol. 11(1993) pp. 15–19.

Mahmood Mirhoseini et al. "Transmyocardial Laser Revascularization: A Review" Journal of Clinical Laser Medicine & Surgery. vol. 11(1993) pp. 15–19.

*Primary Examiner*—Marvin M. Lateef
*Assistant Examiner*—Eleni Mantis Mercader
(74) *Attorney, Agent, or Firm*—Louis J. Capezzuto

(57) ABSTRACT

A medical probe such as a catheter (20) is guided within the body of a patient by determining the relative positions of the probe relative to another probe, as by transmitting non-ionizing radiation to or from field transducers (30, 230) mounted on both probes. In one embodiment, a site probe (28) is secured to a lesion within the body, and an instrument probe (200) for treating the lesion may be guided to the lesion by monitoring relative positions of the probes. Two or more probes may be coordinated with one another to perform a medical procedure.

31 Claims, 13 Drawing Sheets

U.S. PATENT DOCUMENTS

| | | | |
|---|---|---|---|
| 4,054,881 | 10/1977 | Raab | 343/112 R |
| 4,560,930 | 12/1985 | Kouno | 324/207 |
| 4,570,354 | 2/1986 | Hindes | 33/534 |
| 4,592,356 | 6/1986 | Gutierrez | 128/339 |
| 4,613,866 | 9/1986 | Blood | 343/448 |
| 4,642,786 | 2/1987 | Hansen | 364/559 |
| 4,651,436 | 3/1987 | Gaal | 33/533 |
| 4,710,708 | 12/1987 | Rorden et al. | 324/207 |
| 4,788,987 | 12/1988 | Nickel | 128/777 |
| 4,849,692 | 7/1989 | Blood | 324/208 |
| 4,869,238 | 9/1989 | Opie et al. | 128/6 |
| 4,905,698 | 3/1990 | Strohl, Jr. et al. | 128/653 R |
| 4,917,095 | 4/1990 | Fry et al. | 128/660.03 |
| 4,921,482 | 5/1990 | Hammerslag et al. | 604/95 |
| 4,931,059 | 6/1990 | Markham | 606/185 |
| 4,945,305 | 7/1990 | Blood | 324/207.117 |
| 5,002,137 | 3/1991 | Dickinson et al. | 175/19 |
| 5,042,486 | 8/1991 | Pfeiler et al. | 128/653 R |
| 5,059,197 | 10/1991 | Urie et al. | 604/164 |
| 5,078,144 | 1/1992 | Sekino et al. | 128/660.03 |
| 5,099,845 | 3/1992 | Besz et al. | 128/653.1 |
| 5,125,924 | 6/1992 | Rudko | 606/12 |
| 5,125,926 | 6/1992 | Rudko et al. | 606/19 |
| 5,158,084 | 10/1992 | Ghiatas | 128/657 |
| 5,172,056 | 12/1992 | Voision | 324/207.17 |
| 5,195,540 | 3/1993 | Shiber | 128/898 |
| 5,195,968 | 3/1993 | Lundquist et al. | 604/95 |
| 5,197,482 | 3/1993 | Rank et al. | 128/749 |
| 5,211,165 | 5/1993 | Dumoulin et al. | 128/653.1 |
| 5,215,680 | 6/1993 | D'Arrigo | 252/307 |
| 5,217,484 | 6/1993 | Marks | 606/200 |
| 5,234,426 | 8/1993 | Rank et al. | 606/1 |
| 5,251,635 | 10/1993 | Dumoulin et al. | 128/653.1 |
| 5,253,647 | 10/1993 | Takahashi et al. | 128/653.1 |
| 5,255,680 | 10/1993 | Darrow et al. | 128/653.1 |
| 5,265,610 | 11/1993 | Darrow et al. | 128/653.1 |
| 5,267,960 | 12/1993 | Hayman et al. | 604/106 |
| 5,273,025 | 12/1993 | Sakiyama et al. | 128/6 |
| 5,275,166 | 1/1994 | Vaitekunas et al. | 128/660.03 |
| 5,295,484 | 3/1994 | Marcus et al. | 128/660 |
| 5,295,486 | 3/1994 | Wollschager et al. | 128/661.01 |
| 5,301,682 | 4/1994 | Debbas | 128/737 |
| 5,309,913 | 5/1994 | Kormos et al. | 128/653 |
| 5,325,873 | 7/1994 | Hirschi et al. | 128/899 |
| 5,368,564 | 11/1994 | Savage | 604/95 |
| 5,368,592 | 11/1994 | Stern et al. | 606/33 |
| 5,373,849 | 12/1994 | Maroney et al. | 128/662 |
| 5,375,596 | 12/1994 | Twiss et al. | 128/653.1 |
| 5,377,678 | 1/1995 | Dumoulin et al. | 128/653.1 |
| 5,380,316 | 1/1995 | Aita et al. | 606/7 |
| 5,383,454 | 1/1995 | Bucholz | 128/653.1 |
| 5,383,874 | 1/1995 | Jackson et al. | 606/1 |
| 5,383,923 | 1/1995 | Webster, Jr. | 607/125 |
| 5,385,148 | 1/1995 | Lesh et al. | 128/662.06 |
| 5,389,096 | 2/1995 | Aita et al. | 606/15 |
| 5,391,199 | 2/1995 | Ben Haim | 607/122 |
| 5,403,356 | 4/1995 | Hill et al. | 607/14 |
| 5,404,297 | 4/1995 | Birk et al. | 362/421 |
| 5,409,004 | 4/1995 | Sloan | 128/657 |
| 5,423,321 | 6/1995 | Fontenot | 128/664 |
| 5,425,367 | 6/1995 | Shapiro et al. | 128/653 |
| 5,425,382 | 6/1995 | Golden et al. | 128/899 |
| 5,429,132 | 7/1995 | Guy et al. | 128/653.1 |
| 5,431,168 | 7/1995 | Webster, Jr. | 128/658 |
| 5,433,198 | 7/1995 | Desai | 128/642 |
| 5,437,277 | 8/1995 | Dumoulin et al. | 128/653.1 |
| 5,443,489 | 8/1995 | Ben-Haim | 607/115 |
| 5,450,846 | 9/1995 | Goldreyer | 128/642 |
| 5,465,717 | 11/1995 | Imran et al. | 128/642 |
| 5,471,982 | 12/1995 | Edwards et al. | 128/642 |
| 5,471,988 | 12/1995 | Fujio et al. | 128/660.03 |
| 5,480,422 | 1/1996 | Ben-Haim | 607/122 |
| 5,483,951 | 1/1996 | Frassica et al. | 600/104 |
| 5,487,391 | 1/1996 | Panescu | 128/699 |
| 5,538,008 | 7/1996 | Crowe | 128/751 |
| 5,554,152 | 9/1996 | Aita et al. | 606/7 |
| 5,555,883 | 9/1996 | Avitall | 128/642 |
| 5,558,091 | 9/1996 | Acker et al. | 128/653.1 |
| 5,558,092 | 9/1996 | Unger et al. | 128/660.03 |
| 5,577,502 | 11/1996 | Darrow et al. | 128/653.1 |
| 5,588,432 | 12/1996 | Crowley | 128/660.03 |
| 5,617,857 | 4/1997 | Chader et al. | 128/653.1 |
| 5,622,169 | 4/1997 | Golden et al. | 128/653.1 |
| 5,715,822 | 2/1998 | Watkins et al. | 128/653.5 |
| 5,729,129 | 3/1998 | Acker | 324/207.12 |

FOREIGN PATENT DOCUMENTS

| | | |
|---|---|---|
| WO 95/05773 | 3/1995 | (WO) . |
| WO 95/07657 | 3/1995 | (WO) . |
| WO 95/09562 | 4/1995 | (WO) . |
| WO 95/10226 | 4/1995 | (WO) . |
| WO 95/19738 | 7/1995 | (WO) . |
| WO 96/05768 | 2/1996 | (WO) . |
| WO 96/41119 | 12/1996 | (WO) . |
| WO 97/03609 | 2/1997 | (WO) . |
| WO 97/29678 | 8/1997 | (WO) . |
| WO 97/29679 | 8/1997 | (WO) . |
| WO 97/29683 | 8/1997 | (WO) . |
| WO 97/29684 | 8/1997 | (WO) . |
| WO 97/29685 | 8/1997 | (WO) . |
| WO 97/29701 | 8/1997 | (WO) . |
| WO 97/29709 | 8/1997 | (WO) . |
| WO 97/29710 | 8/1997 | (WO) . |
| WO 97/29803 | 8/1997 | (WO) . |
| WO 97/32179 | 9/1997 | (WO) . |

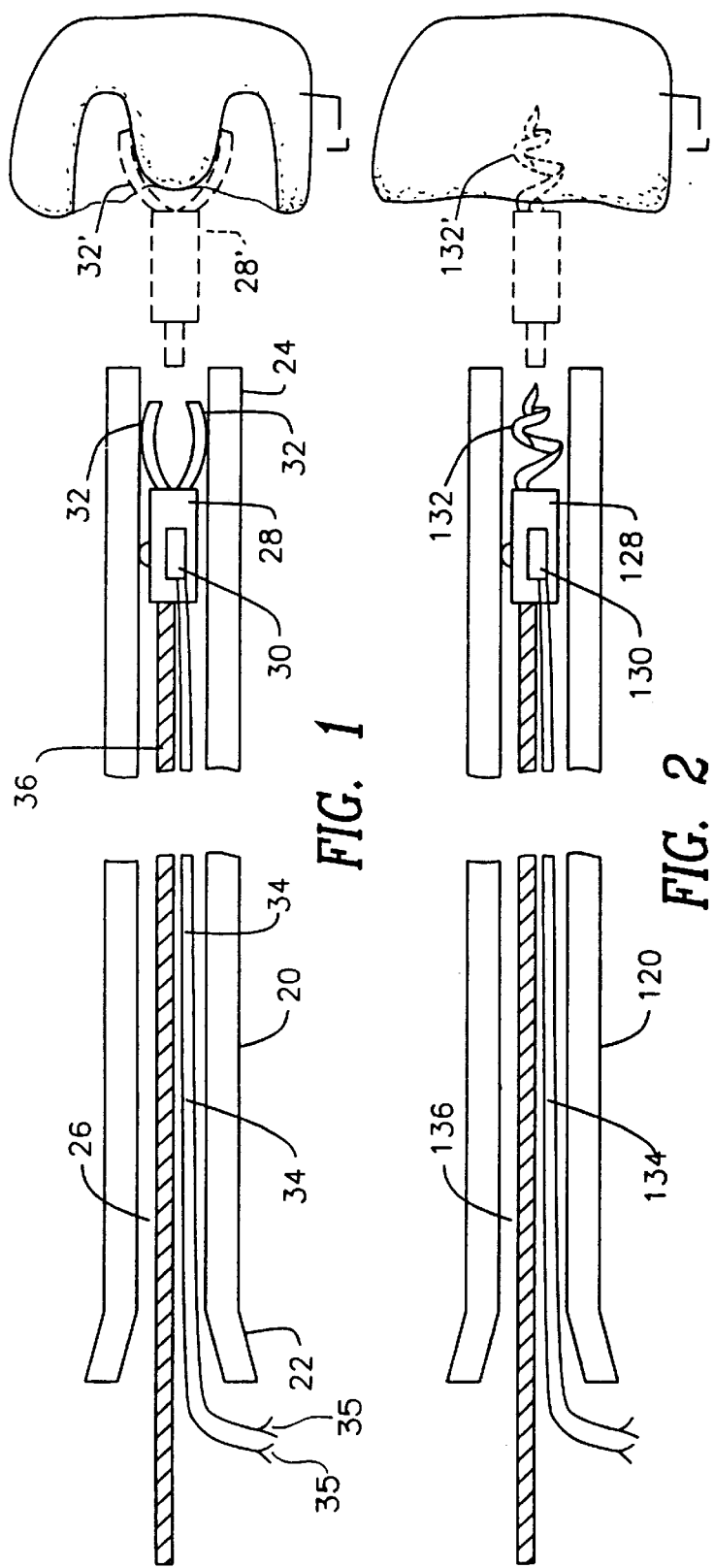

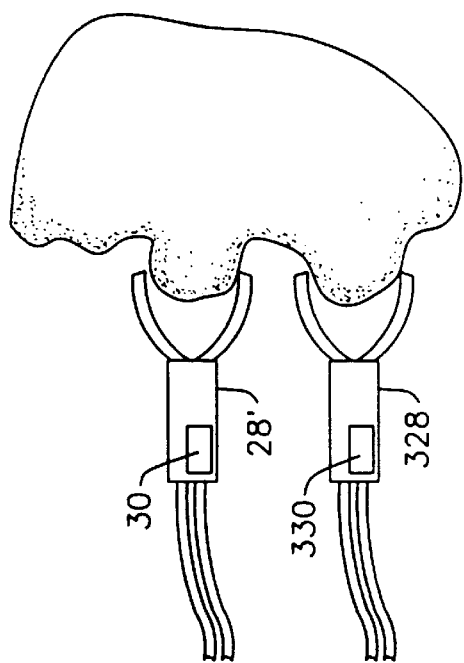
FIG. 8
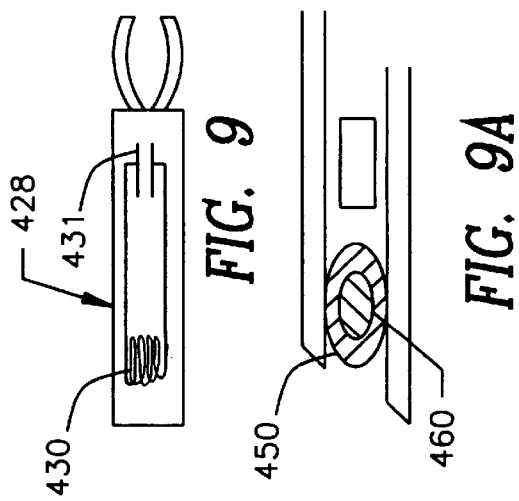
FIG. 9
FIG. 9A
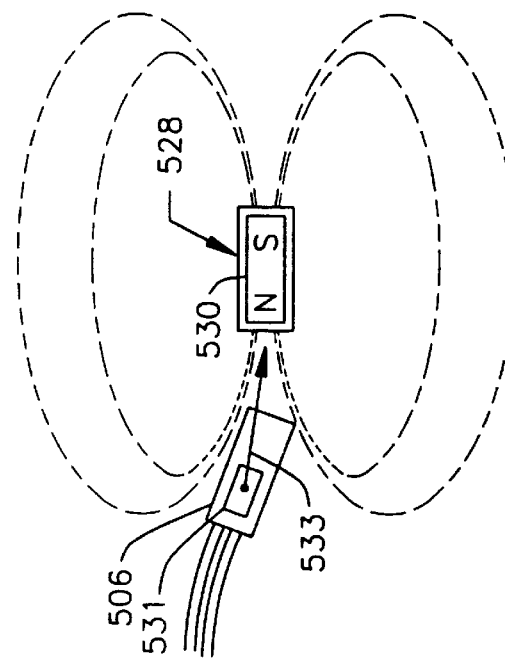
FIG. 10

MEDICAL PROCEDURES AND APPARATUS USING INTRABODY PROBES

CROSS REFERENCE TO RELATED APPLICATIONS

The present application claims benefit and priority of the following five applications, and the disclosures of all of such applications are incorporated by reference herein:
U.S. application Ser. No. 60/012,275, filed Feb. 26, 1996
U.S. application Ser. No. 60/011,721, filed Feb. 15, 1996
U.S. application Ser. No. 60/031,824, filed Nov. 26, 1996,
Israel 119,262, filed Sep. 17, 1996
Israel 119,137, filed Aug. 26, 1996
The following PCT applications, each of which names Biosense, Inc as an applicant are also incorporated by reference herein: Catheter Based Surgery filed on or about Feb. 14, 1997 in the Israeli Receiving Office; Intrabody Energy Focusing filed on or about Feb. 14, 1997 in the Israeli Receiving Office; Locatable Biopsy Needle, filed on or about Feb. 14, 1997 in the Israeli Receiving Office; Catheter Calibration and Usage Monitoring filed on or about Feb. 14, 1997 in the Israeli Receiving Office; Precise Position Determination of Endoscopes filed on or about Feb. 14, 1997 in the Israeli Receiving Office; Medical Probes with Field Transducers filed Feb. 14, 1997 in the United States Receiving Office; Catheter with Lumen filed Feb. 14, 1997 in the United States Receiving Office; Movable Transmit or Receive Coils for Location System filed Feb. 14, 1997 in the United States Receiving Office; and Independently Positionable Transducers for Location System filed Feb. 14, 1997 in the United States Receiving Office. The PCT application entitled, Multi-Element Energy Focusing, filed Feb 14, 1996 in the Israeli Receiving Office and naming Victor Spivak as applicant is also incorporated by reference herein.

TECHNICAL FIELD OF THE INVENTION

The present invention relates to medical probes having sensors for detecting the disposition of the probe, and to the medical procedures utilizing such probes.

BACKGROUND ART

Conventional surgical procedures involve cutting through bodily structures to expose a lesion or organ within the body for treatment. Because these procedures create considerable trauma to the patient, physicians have developed minimally invasive procedures using probes inserted into the body through body orifices or through small holes to treat or measure structures within the body. For example, the devices commonly referred to as endoscopes include an elongated body having a distal end and a proximal end. The distal end of the probe body can be inserted into the gastrointestinal tract through a body orifice. The endoscope may be equipped with optical devices such as cameras or fiber optics to permit observation of the tissues surrounding the distal end, and surgery may be performed by inserting and maneuvering surgical instruments through a channel in the endoscope body. Other probes commonly referred to as laparoscopes and orthoscopes are inserted into the body through small holes formed in surrounding tissues to reach the bodily structures to be treated or measured. Still other probes, commonly referred to as catheters, can be advanced through the vascular system, as through a vein or artery, or through other bodily passages such as the urinary tract.

The physician can guide the probe to the desired location within the body by feel or by continuously imaging the probe and the body, as by fluoroscopy, during the procedure. Where the probe includes optical elements, the physician can guide the probe based on visual observation of the tissues surrounding the distal tip of the probe. However, this option is available only for probes such as conventional endoscopes which are large enough to accommodate the optical elements. Moreover, optical guidance normally is useful only where the distal tip of the probe is disposed within a cavernous organ; it is not normally useful in guiding the probe within solid or semisolid tissues.

As described, for example, in U.S. Pat. Nos. 5,558,091, 5,391,199; 5,443,489; and in PCT International Publication WO 96/05768, the disclosures of which are hereby incorporated by reference herein, the position, orientation or both of the distal end of a probe can be determined by using one or more field transducers such as a Hall effect or magnetoresistive device, coil or other antenna carried on the probe, typically at or adjacent the distal end of the probe. One or more additional field transducers are disposed outside the body in an external frame of reference. The field transducers preferably are arranged to detect or transmit non-ionizing fields or field components such as a magnetic field, electromagnetic radiation or acoustical energy such as ultrasonic vibration. By transmitting the field between the external field transducers and the field transducers on the probe, characteristics of field transmission between these devices can be determined. The position and/or orientation of the sensor in the external frame of reference can then be deduced from these transmission characteristics. Because the field transducer of the probe allows determination of the position of the probe, such transducer is also referred to as a "position sensor".

As described, for example, in the aforementioned U.S. Pat. No. 5,558,091, the frame of reference of the external field transducers can be registered with the frame of reference of imaging data such as magnetic resonance imaging data, computerized axial tomographic data, or conventional x-ray image data and hence the position and orientation data derived from the system can be displayed as a representation of the probe superimposed on an image of the patient's body. The physician can use this information to guide the probe to the desired location within the patient's body, and to monitor its orientation during treatment or measurement of the body structure. This arrangement greatly enhances the ability of the physician to navigate the distal end of the probe through bodily structures. It offers significant advantages over conventional methods of navigating probes by feel alone. For instance, because it does not require acquisition of an optical image of the surrounding tissues for navigation purposes, it can be used with probes which are too small to accommodate optical elements, and can be used for navigation of the probe within solid or semisolid tissues. The transducer-based system also avoids the difficulties associated with navigation of a probe by continuous imaging of the probe and patient during the procedure. For example, it avoids exposure to ionizing radiation inherent in fluoroscopic systems.

As described in certain embodiments taught in U.S. Pat. No. 5,391,199, the system can include one or more reference catheters and a mapping/ablation catheter. Each of these catheters has a field transducer as discussed above disposed adjacent the distal end of the catheter. The mapping/ablation catheter is provided with electrodes for detecting local electrical activity at the distal end of such catheter, and for applying radio frequency energy to ablate surrounding tissue. The reference catheters may be positioned with their distal tips at fixed locations within the heart, whereas the mapping/ablation catheter can be moved within the heart while measuring electrical activity. The tip positions of the reference catheter and of the mapping/ablation catheter are monitored in the frame of reference of external antennas. Electrical activity data and positional data provided by the mapping/ablation catheter provides a map of the electrical activity of the heart. The reference catheter position information can be used to compensate for movement of the heart, and to register the mapping/ablation catheter position data with images such as fluoroscopic or MRI images. In certain procedures taught in the '199 patent, the map can be used to locate a site within the heart for treatment, and the position information provided by the position sensors can be used to maneuver the mapping/ablation catheter to the treatment site.

However, still further improvements in transducer-based probe navigation and treatment systems would be desirable. In particular, it would be desirable to provide accurate guidance of a probe without reliance on registration between the sensor-based positional data and previously-acquired image data. This would be particularly desirable for placement and treatment of a probe in relatively soft, mobile tissues such as the breasts, lungs, liver, gastrointestinal tract and other internal organs. Moreover, it would be desirable to provide a system which provides probe guidance information to the physician in a form which can be readily assimilated and used by the physician. It would also be desirable to provide a system which facilitates the use of multiple probes in combination to treat, observe or measure a body structure.

DISCLOSURE OF THE INVENTION

The present invention addresses these needs.

One aspect of the present invention provides methods of guiding medical instruments. A method according to this aspect of the invention desirably includes the steps of providing a site probe at a site within the body of a patient and providing an instrument probe to be guided within the body of the patient. The method further desirably includes the step of transmitting one or more fields to or from each of the probes and detecting each such transmitted field. The relative disposition of the site probe and the instrument probe is determined from the properties of the detected fields and the instrument probe is directed toward the site probe on the basis of the so determined relative disposition. As used in this disclosure with reference to a single probe, the term "disposition" refers to the position of the probe, the orientation of the probe, or both. As used in this disclosure with reference to any two probes, the term "relative disposition" refers to the direction from one probe to the other, the distance from one probe to the other, or both. Thus, in determining relative disposition, the direction from one probe to the other, or the distance from one probe to the other can be determined. Preferably, however, both direction and distance are determined so as to completely determine the relative positions of the two probes. The orientations of one or both probes may also be determined.

For example, magnetic, electromagnetic or acoustic fields may be transmitted between external field transducers and field transducers on the site and instrument probes, so that the position of each such probe is determined in a common frame of reference provided by the external transducers. The position of the instrument probe relative to the site probe can be determined by subtracting the position vectors of the two probes in the external antenna frame of reference. The step of directing the instrument probe relative to the site probe may include the step of pointing the instrument probe in a particular direction relative to the site probe, such as pointing the instrument probe in a direction toward the site probe. Preferably, the step of directing the instrument probe toward the site probe in response to the determined relative disposition includes the step of moving the instrument probe in a particular direction relative to the site probe, most preferably moving the instrument probe toward the site probe. In preferred methods according to this aspect of the invention, the site probe acts as a marker and the instrument probe is guided toward the marker.

The step of determining the relative dispositions of the probes may include the step of transmitting a field from the position sensor on one probe to the position sensor on another probe and determining the relative dispositions based upon the characteristics of such transmission. For example, the position sensor on the site probe may be arranged to emit electromagnetic or ultrasonic radiation, whereas the position sensor on the instrument probe may be arranged to monitor the amplitude of radiation received at the tip of the instrument probe. The amplitude of the received radiation constitutes a measure of the distance between the probes.

Alternatively, the relative dispositions of the probes can be determined by monitoring fields transmitted between the probes. For example, the site probe field transducer may include or consist of a permanent magnet arranged to provide a magnetic field. The instrument probe field transducer may be adapted to determine the direction of the magnetic fields prevailing at the distal end of the instrument probe, thereby providing an indication of the direction from the instrument probe to the site probe. The intensity of the magnetic field can be used an indication of distance from the site probe in such an arrangement. In yet another arrangement, the site probe may be arranged to emit ultrasonic or electromagnetic radiation. The instrument probe may be guided to the site probe by moving it in the direction of increasing field amplitude. The instrument probe may be provided with a field transducer capable of detecting the amplitude of such radiation. The site probe may include a guidewire or other elongated member and the site probe may emit the field along the length of such elongated member.

In a particularly preferred arrangement, the site probe is placed at a site which requires treatment, testing or another medical procedure. For example, the site probe may be placed in or near a lesion during an imaging procedure such as mammography or other x-ray procedures, magnetic resonance imaging or CAT scanning capable of imaging the lesion and the site probe. After the site probe is placed, a surgical procedure to remove or repair the lesion may be performed by moving the distal end of an instrument probe toward the site probe and performing the required treatment using the instrument probe. As the site probe is anchored in the patient's tissue in or adjacent the lesion, the instrument probe can be guided accurately to the lesion even if the patient's tissues shift or deform. It is not necessary to image the patient during the treatment procedure. Therefore, the treatment procedure can be conducted without the physical encumbrance of the imaging apparatus and without exposing the physician or patient to additional radiation from the imaging apparatus.

In another preferred embodiment, a device implanted within the patient for long-term treatment purposes may be provided with a field transducer so that the device can be located and removed. For example, the heart pacemaker leads, which are implanted within a patient, sometimes break, leaving the distal portion of the lead implanted in the patient. Each such lead may be provided with a field transducer before implantation, so that the detached lead portion can be located and removed in the same manner as the lesions discussed above.

In a further preferred embodiment, a passageway such as a fistula or shunt can be formed within a bodily structure by placing the site probe at an ending location corresponding to one end of the desired passageway; placing the instrument probe at a starting location corresponding to the opposite end of the desired passageway and then moving the instrument probe through the tissues to be penetrated while guiding the motion of the instrument probe toward the site probe using the detected relative positions of the two probes. In effect, the site probe serves as a target and the passageway is formed by moving the instrument probe through the tissues toward the target. In a variant of this approach, the instrument probe is pointed toward the site probe and a substance or energy capable of destroying tissue is emitted from the instrument probe toward the site probe, thereby boring the hole from the starting location to the ending location.

Yet a further aspect of the present invention provides a method of making a intrahepatic portal-systemic shunt, i.e., a shunt from the hepatic vein to the portal vein. Such shunts have been provided heretofore to relieve blockage of the portal vein arising from cirrhosis or other disease of the liver. Such a shunt serves to reduce the elevated venous pressure prevailing in this condition. According to this aspect of the present invention, an instrument probe such as a needle is guided from a starting location in the hepatic vein or the portal vein to an ending location in the opposite one of these veins, i.e., from the hepatic vein to the portal vein or from the portal vein to the hepatic vein. The guidance is performed using a field transducer on the instrument probe and using non-ionizing fields transmitted to or from such field transducer. In one arrangement according to this aspect of the invention, a site probe as discussed above is positioned at the ending location, i.e., in or near the portal vein or the hepatic vein and the needle or instrument probe is guided toward the ending location on the basis of the relative positions of the site probe and instrument probe. In another arrangement, the instrument probe position can be determined in a frame of reference such as the frame of reference of external field transducers and the positional information can be registered with a previously acquired image of the liver, so that a representation of the needle can be superimposed on an image of the liver. Still further aspects of the present invention include methods of treating tissues within the lungs by guiding an instrument probe such as a bronchoscope within the lung using non-ionizing fields transmitted to or from the instrument probe. Preferred methods according to this aspect of the present invention utilize a site probe disposed in the lung tissue at or near the location to be treated, and provide guidance by monitoring the relative position of the instrument probe and site probe.

Yet another aspect of the present invention provide methods of performing medical procedures using two or more probes. Methods according to this aspect of the present invention include the step of providing first and second probes, each probe having a field transducer mounted thereon, and determining the relative dispositions of the two probes. Methods according to this aspect of the invention preferably further include the steps of determining the relative dispositions of the two probes using non-ionizing fields transmitted to or from the position sensors on the probes; performing a first medical procedure with the first probe and a second medical procedure with the second probe and coordinating the two medical procedures using the determined relative dispositions. For example, where the medical procedure performed by the first probe involves tunneling, cutting or excavating tissues, the medical procedure performed by the second probe may include imaging, of the region treated by the first probe; evacuation of debris from the region treated by the first probe or any other procedure which can benefit by maintaining the two probes in defined spatial relationship to one another.

Yet another aspect of the present invention provides methods of performing medical procedures which also use first and second probes. Procedures according to this aspect of the present invention include the steps of providing first and second probes, each having a field transducer thereon; performing a medical procedure at a location using the first probe; determining the relative positions of the probes and performing a medical procedure at a second location having a predetermined spatial relationship to the first location using the second probe. In this procedure, localization of the medical procedure performed by the second probe is based on the determined relative dispositions of the two probes. That is, the region of the patient's body treated, measured or imaged in the second medical procedure may be selected or controlled based upon the relative dispositions of the two probes. Provided that the first probe is located in the required disposition relative to the body of the patient, both probes will be in the required disposition relative to a structure in the body of the patient, and relative to one another. The first and second locations may be identical to one another, so that both probes act at the same point. The first and second locations may be different from one another, in which case the first and second locations may be related to a common body structure. For example, where the first probe is positioned at a point along an intrabody lumen such as an artery or vein, the relative disposition of the first and second probe may be selected so that the second probe is disposed at another point in the same artery or vein. In each of the aforesaid methods, additional probes having field transducers thereon may be employed as well.

Yet another aspect of the present invention provides a site probe for marking a site within the body of a medical patient. A site probe according to this aspect of the present invention preferably includes a field transducer in the form of a sensor adapted to detect a non-ionizing field such as a magnetic or electromagnetic field or an acoustic field and to provide one or more sensor signals representing one or more properties of the so detected fields. The site probe according to this aspect of the present invention may further include an anchor adapted to fasten the field transducer to tissue within the body of the living patient and signal transmission means for conveying the sensor signals from within the body of the patient to outside of the body of the patient.

Alternatively, a site probe for marking a site within the body of a patient may include a field transducer which incorporates an antenna or other transducer adapted to transmit a non-ionizing field in response to one or more drive signals, a site probe body housing the device, and an anchor adapted to fasten the site probe body to tissue within the body of the patient. A site probe according to this aspect of the present invention preferably includes signal transmission means for transmitting the drive signals from outside the body of the patient to the device while the device is disposed within the body of the patient.

The anchor may include a mechanical device such as a screw having threads adapted to engage tissue or a pincer incorporating a plurality of flexible or movable times adapted to engage tissue within the patient's body. The site probe as described above may be provided in an assembly together with an elongated probe such as a catheter having distal and proximal ends. The site probe may be releasably mounted to the elongated probe adjacent the distal end thereof so that the site probe can be advanced within the body of the patient while the proximal end of the elongated probe remains outside of the body, anchored to the patient tissue at a desired location within the body and left within the patient's body. The signal transmission means incorporated in the site probe may include one or more leads extending from the sensor towards the proximal end of the elongated probe, these leads being arranged so that the elongated probe can be withdrawn leaving the leads in position after the site probe has been fastened to the tissue by the anchor.

Further aspects of the present invention provide apparatus for guiding an instrument to a site within a patient comprising a site probe as aforesaid and an instrument probe adapted for insertion within the body. The instrument probe has a field transducer mounted thereon adapted to send or receive fields of the type sent or received by the site probe. The apparatus may further include one or more external field transducers adapted for disposition outside of the patient's body and drive means for actuating the field transducers of the site probe, the instrument probe and, where provided, the external field transducers to transmit one or more non-ionizing fields therebetween and detect each so-transmitted field. As discussed above in connection with the method, the relative dispositions of the instrument probe and site probe may be determined from the detected fields.

These and other objects, features and advantages of the present invention will be more readily apparent from the detailed description of the preferred embodiments, taken in conjunction with the accompanying claims.

BRIEF DESCRIPTION OF THE DRAWINGS

FIG. 1 is a diagrammatic view depicting a probe in accordance with one embodiment of the invention.

FIG. 2 is a view similar to FIG. 1 but depicting a probe in accordance with a further embodiment of the invention.

FIG. 3 is a fragmentary view depicting a probe in accordance with yet another embodiment of the invention.

FIG. 8 is a fragmentary diagrammatic view depicting elements of apparatus in accordance with yet another embodiment of the invention.

FIG. 9 is a fragmentary diagrammatic view depicting elements of apparatus in accordance with a further embodiment of the invention.

FIG. 9A is a fragmentary diagrammatic view depicting elements of apparatus in accordance with a another embodiment of the invention.

Each one of FIGS. 10 through 17 is a fragmentary, diagrammatic view depicting apparatus and portions of a patient during procedures in accordance with a further embodiment of the invention

MODES FOR CARRYING OUT THE INVENTION

Figure 4:
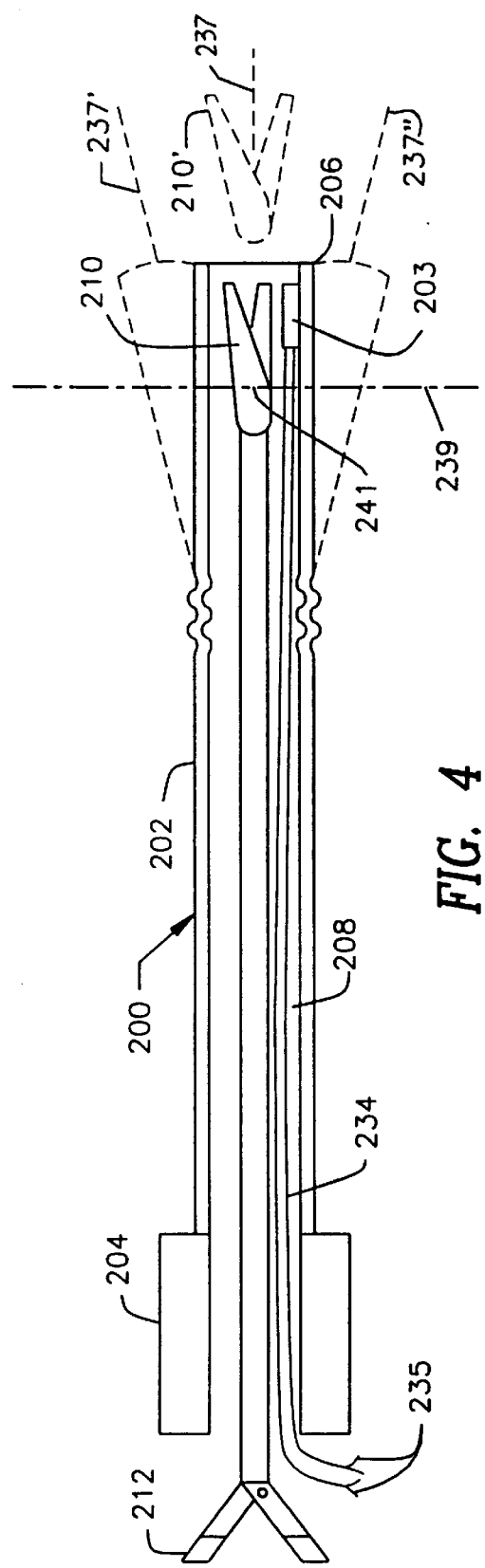
FIG. 4 is a view similar to FIG. 1 but depicting a probe in accordance with yet another embodiment of the invention.

A site marking probe assembly in accordance with one embodiment of the invention includes an elongated probe in the form of a tube or catheter 20 having a proximal end 22, a distal end 24 and an elongated bore 26 extending between such ends. A site probe body 28 incorporating a position sensor or field transducer 30 is physically connected to an anchor in the form of a set of hooks or grapples 32. Field transducer 30 is provided in the form of a sensor arranged to detect magnetic or electromagnetic fields. For example, the sensor 30 may be a multiaxis, solid-state position sensor of the type disclosed in the aforementioned U.S. Pat. No. 5,558,091. Such a sensor incorporates a plurality of transducers sensitive to magnetic field components in mutually orthogonal directions. Other suitable position sensors include coils as disclosed in the aforementioned U.S. Pat. No. 5,391,199 and in PCT Application PCT/US95/01103, now published as PCT International Publication WO 96/05768, the disclosure of which is hereby incorporated herein by reference. Such coils may be provided as a single coil or as a plurality of orthogonal coils capable of detecting field components in orthogonal directions. Position sensor or field transducer 30 is connected to leads 34 which extend through bore 26 to and beyond the proximal end 22 of tube 20. Connectors 35 are provided at the proximal ends of leads 34. A control rod 36 in the form of a flexible shaft extends axially within bore 26 from outside the proximal end 22 of the tube to the site probe body 28. Control rod 36 may be a braided cable or other flexible element capable of bending and deforming along with tube 20, but also capable of transmitting axial thrust. Elongated probe or tube 20 is constructed and arranged to reach within the body of the patient to the desired location. For example, tube 20 may have the structure of a conventional catheter, bronchoscope, endoscope, laparoscope or the like. The size and shape of tube 20 will depend upon the region of the body to be treated. Tube 20 may be steerable or guidable, and may be provided with features as discussed below for selectively bending its distal end.

Site probe body 28 is releasably engaged within bore 26 adjacent distal end 24 so that the body 28 and hence grapples 32 can be displaced out of the distal end 24 of the tube. Grapples 32 are spring-loaded so that they tend to expand to the positions indicated in broken lines at 32' in FIG. 1 when the device is displaced out of the distal end of the tube. The spring-loaded grapples 32 may provide frictional engagement with the wall of tube 20 while the device is disposed inside the tube and thus may serve to releasably retain the device in the tube. As further discussed below, in use the assembly is advanced until distal end 24 is disposed adjacent a lesion L or other tissue of interest within the patient's body. At that point, body 28 and anchor or grapples 32 are advanced forwardly by control rod 36, thereby dislodging the device from within tube 20 and engaging grapples 32 with the tissue of lesion L at the distal end of the assembly as indicated at 32'. In this condition, site probe body 28, and hence sensor or field transducer 30 are secured to the tissue of lesion L by the grapples.

Tube 20 may be removed, leaving control rod 36 and leads 34 in place. During the removal process, the tube 20 slides in a proximal direction over control rod 36, leads 34 and connectors 35, so that the control rod and leads pass out of the distal end 24 of bore 26. To facilitate movement of the control rod and leads through the bore tube, the control rod and the leads may be formed integrally with one another. Also, although only tube leads are depicted in FIG. 1, it should be appreciated that the number of leads will depend upon the configuration of position sensor 30.

An assembly according to a further embodiment of the invention (FIG. 2) incorporates a tube 120, site probe body 128; sensor or field transducer 130; control rod 136 and leads 134 similar to the corresponding elements of the assembly in FIG. 1. However, this assembly includes an anchor in the form of a screw 132 in place of the grapples used in the embodiment of FIG. 1. In use, control rod 136 is used to turn active element 128 and hence screw 132 while forcing active element out of the interior of tube 120, thereby leaving the active element anchored to the tissue by the screw as indicated in broken lines at 132'.

As indicated in FIG. 3, the screw or grapples can be replaced by a needle 140 affixed to the active element body. The needle is provided with a barb 142. Here again, the active element body and the anchor are forced distally out of the distal end 124 of the tube so that the anchor engages the tissue. Barb 142 holds the active element body and sensor in place. Assemblies according to this aspect of the invention may include many different forms of anchors, in addition to the barbs, screws and grapples discussed above. Various devices which can be implanted and mechanically engaged in the tissue of a patient are shown in U.S. Pat. Nos. 5,217,484; 5,195,540; 4,592,356; 4,931,059; 5,234,426; 5,267,960; 5,409,004; 5,158,084; 5,059,197; 5,197,482; and 5,301,682. All of these patents teach mechanical devices for fastening a device to the tissue of a patient, for marking a lesion or for other purposes. Essentially any mechanical device which can be actuated to anchor the active device body to the patient's tissue can be employed as the anchoring device in structures as depicted in FIGS. 1–3. Further, although it is preferred to insert the active device body through a tubular element as shown, the same is not essential. For example, the site probe may incorporate a site probe body in the form of a rigid needle housing the field transducer so that the needle, with the position sensor disposed adjacent the distal end of the needle, can be advanced into the body. Such a needle can be placed by itself, without any external covering, by advancing the needle into the patient's tissues. Such a rigid needle can be provided with anchors as discussed above to hold the needle in place after insertion in a method according to one embodiment of the invention. Similarly, the site probe body can be integrated with the elongated flexible bodies discussed above. For example, transducer 30 and grapples 32 (FIG. 1) could be mounted to elongated probe body 20, in which case the elongated probe body would be left in place.

Apparatus according to the present invention preferably also includes an instrument probe 200 (FIG. 4). The instrument probe may incorporate essentially any device which can be inserted or advanced into the body to perform a medical procedure, such as treatment, measurement or observation. As used herein, the term "treatment" includes capturing samples of tissues or materials present within the body, and thus includes biopsies. As illustrated, instrument probe 200 includes a tubular body 202 having a handle portion 204 affixed to a proximal end of the body and having a distal portion 206 remote from handle 204. Body 202 has a bore 208 extending longitudinally from its proximal end to its distal end and open to the outside through handle 204. Body 202 may incorporate a flexible section adjacent the distal end, so that the distal end 206 can be bent or pivoted relative to the remainder of the body. The body of the instrument probe defines a long axis 237 at end 206, and axes 239 and 241 orthogonal to axis 241. Probe 200 may incorporate devices (not shown) for bending the distal end of body 202 relative to the remainder of the body and thereby steer the device as it is advanced into the patient's anatomy. Movement of end 206 around axis 237 is commonly referred to as "roll", whereas movements of the end around axes 239 and 241, such as encountered during bending of the body or during tilting of the entire device, are referred to as "pitch" and "yaw" respectively. These elements of the instrument probe may be substantially conventional, and may be of the types commonly utilized in steerable catheters, needles, endoscopes and other probes. Bore 208 is arranged to accommodate a conventional intrabody medical instrument such as scissors or forceps, or other surgical tool 210 operable from the proximal end or handle of the device. Surgical tool 210 may be any conventional surgical tool of the type commonly used in endoscopic, arthroscopic, laparoscopic surgical procedures, or a conventional biopsy sampling device. The tool is arranged so that it can be advanced to an operative position 210' outside of the distal end of body 202. Tool 210 is arranged so that it can be manipulated and controlled from the proximal end or handle 204 of the body. Thus, the tool is connected to a manipulating handle 212 by conventional control elements or linkages. Other expedients for manipulating and controlling a tool at the distal end of body 202 can be employed as, for example, electrical, electronic or optical control linkages. Alternatively, tool 210 can be mounted in fixed position on body 202 or formed integrally therewith as, for example, where body 202 is equipped with a cutting blade. For example, body 202 may be a biopsy needle of generally conventional construction, or else may be a biopsy needle of the type described in the copending, International Application, entitled "Locatable Biopsy Needle", naming Biosense, Inc. as an applicant and filed in the Israeli Receiving Office on even date herewith, the disclosure of which is hereby incorporated by reference herein. The instrument probe may incorporate a conventional surgical instrument such as a scalpel, forceps, or other instrument having parts which can be advanced into the patient's body to perform a surgical or medical procedure at a place within the patient's body. Tool 210 may be a device for measuring or sensing phenomena within the body, such as a thermometer or electrode for measuring intrabody potentials; a device for imaging structures within the body, such as an optical or ultrasonic camera or other imaging device; a device for dispensing medications; a device for applying therapeutic radiation; or any other device which can be used to treat, measure or observe structures within the body of a living subject.

A field transducer or position sensor 230 is mounted in instrument probe body 202 adjacent the distal end 206 thereof. Transducer 230 may be of the same types as discussed above with reference to the position sensors of the site probes. Transducer 230 is connected via leads 234 to the proximal end or handle 204 of the body. Leads 234 are provided with exposed terminals or connections 235 at the proximal end of the body. If the instrument probe incorporates a rigid or substantially rigid body, the field transducer 230 can be mounted at essentially any location on the body having a defined spatial relationship to the operative portions of the instrument, such that the disposition of the operative portions can be deduced from the disposition of the field transducer. However, where the instrument probe is flexible, the field transducer preferably is mounted adjacent any operative portions of the tool incorporated in the instrument probe, so that the disposition of the operative portions of the tool included in the instrument probe can be deduced from the disposition of the field transducer.

The apparatus further includes a set of field transducers or antennas 300 mounted in a frame of reference external to the patient. For example, field transducers 300 may be mounted to a patient-supporting bed. Antennas 300 are linked to a field transmitting and receiving device 302 and a computer 304, which in turn is linked to a displayed device such as a cathode ray tube 306. These elements are arranged to cooperate with the field transducers or position sensors on the site probe and on the instrument probe to determine the dispositions of the field transducers on the probes, and hence determine the dispositions of the site probe and the instrument probe in the frame of reference of the external field transducers or antennas. These elements of the apparatus can be as described in the aforementioned '091 or '199 patents. Other devices for detecting disposition of probes equipped with position sensors by transmission of non-ionizing fields are known in the art. As is known in the art, electromagnetic or magnetic fields can be transmitted between an antenna or field transducer mounted in an external frame of reference and a position sensor or field transducer on a probe, and the disposition of the probe can be calculated from the characteristics of the fields detected by the transducer on the probe. Thus, the external field transducers or antennas and the position sensor or field transducer on the probe cooperatively define a plurality of transmitter-receiver pairs. Each such pair includes one transmitter and one receiver as elements of the pair. One element of each such pair is disposed on the probe and the other element of each such pair is disposed at a known disposition in the external frame of reference. Typically, at least one element of each transmitter-receiver pair is disposed at a different position or orientation than the corresponding element of the other pairs. By detecting the characteristics of field transmission between elements of the various pairs, the system can deduce information concerning the disposition of the probe in the external frame of reference. The disposition information can include the position of the probe, the orientation of the probe or both.

In a method according to one embodiment of the invention, site probe body 28 is positioned and anchored on a lesion L within the patient's body during a conventional radiologic procedure. For example, while the patient is undergoing fluoroscopic, X-ray or other imaging examination of the lungs, the site probe assembly is advanced to a lesion observed in such examination, and the site probe body 28 is anchored on the lesion using guidance provided by the imaging procedure. The anchoring element such as grapples 32 is actuated to anchor the site probe body in place on the lesion, and the tubular body 20 is withdrawn, leaving leads 34 protruding from the patient's body.

After the site probe has been placed, the patient is positioned in the frame of reference of the external field transducers or antennas 300. Leads 34 are connected to the field transmitting and receiving unit 302, thereby connecting the field transducer or position sensor 30 on the site probe to the transmitting and receiving unit. Similarly, the field transducer or position sensor 230 of the instrument probe (FIG. 4) is connected to the transmit/receive unit 302 through leads 234. The distal end 206 of the instrument probe is advanced into the patient towards the lesion, carrying the position sensor or field transducer 230 with it. The field transmitting and receiving unit 302 and computer 304 actuates external field transducers or antennas 300 and the field transducers or position sensors 30 and 230 of the probes to transmit and receive fields. Where the external devices or antennas 300 are used as field transmitters, the leads 34 and 234 from the probes will provide sensor signals representing the fields detected at the probes to the field transmit and receive unit. Conversely, where the field transducers or position sensors on the probes are used as transmitters, leads 34 and 234 can be used to send drive signals to field transducers or position sensors 30, 230 on the probes. In the conventional manner, the computer 304 deduces the disposition of the field transducers on the probes and thus deduces the disposition of the probes themselves in the frame of reference defined by the external field transducers. In the arrangement shown, the computer deduces the position of probe 28 and causes the same to be displayed at a location 28' on display unit 306 and likewise deduces the position of the distal end 206 of the instrument probe and displays the same at a location 206" on display 306. Display of the two locations provides a visual indication of the distance and direction from the distal end 206 of instrument probe 200 to the site probe body 28. This guides the physician as he or she advances the instrument probe toward the site probe through the patient's tissues.

Because the site probe is mounted in the patient's body at or adjacent to the lesion or other tissue to be treated, the actual position of the lesion or tissue will not affect operation of the system. Thus, the patient can move in the external frame of reference, and the lesion or tissue may move within the patient. For example, the lung being treated may be deflated after placement of the site probe but before the other steps of the procedure. Nonetheless, the system will continue to display the correct position of the instrument probe distal end and the site probe, and will continue to provide proper guidance for navigating the instrument probe towards the lesion or other tissue to be treated. As used in this disclosure, the terms "navigation" and "navigating" refer to the process of moving a probe within the body of a patient to a desired location. During the navigation procedure, the physician may rely on additional information and cues such as his or her knowledge of the anatomy and feel of the instrument probe as the same is advanced through the patient's body. Where conventional visualization devices such as cameras or fiber optic devices are provided on the instrument probe, these may be used to provide additional guidance. Also, the system may augment the display 306 by providing a prominent indication of the direction from the instrument probe distal end to the site probe as, for example, a bold arrow 308 extending in that direction. The indicia representing the instrument probe and the site probe on the display may have different characteristics, such as different colors or shapes, so that the physician can readily distinguish them from one another.

The display need not show any image of the patient's tissues. However, if previously acquired image data is readily available and can be readily registered with the probe position data, the previously acquired image data can be displayed in registration with the indicia representing the probes.

Figure 7:
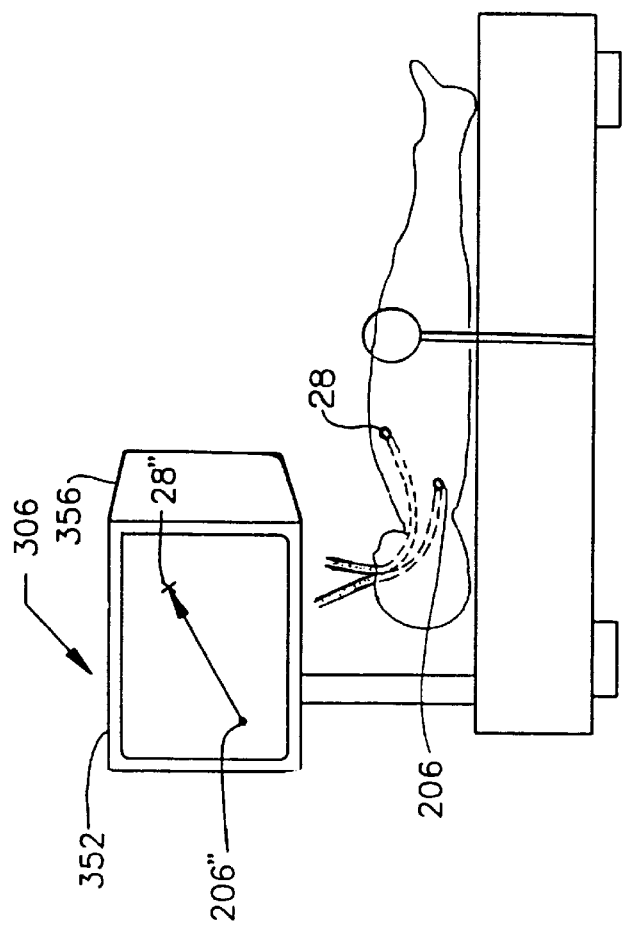
FIG. 7 is an elevational view of the same patient and apparatus of FIG. 6, but taken along a saggital plane.
Figure 6:
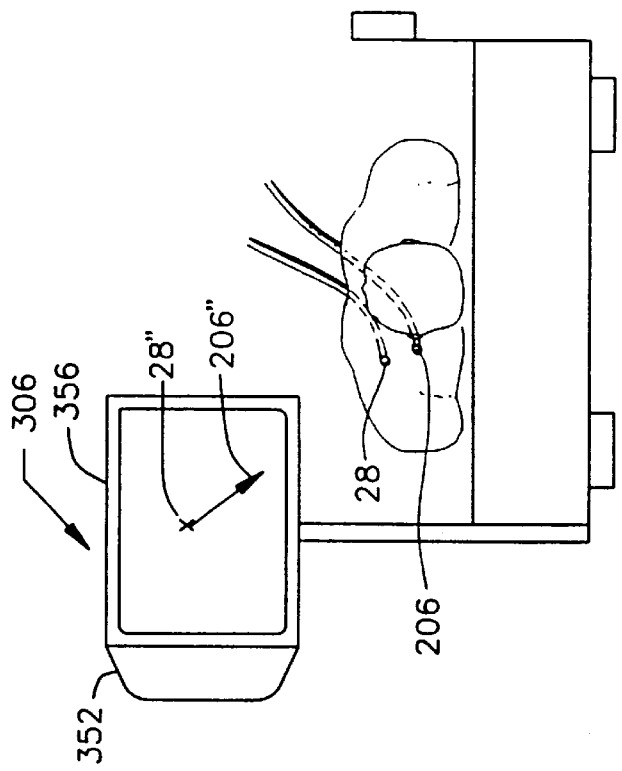
FIG. 6 is a diagrammatic elevational view taken on an axial plane depicting a patient and apparatus during a further process in accordance with another embodiment of the invention.
Figure 11:
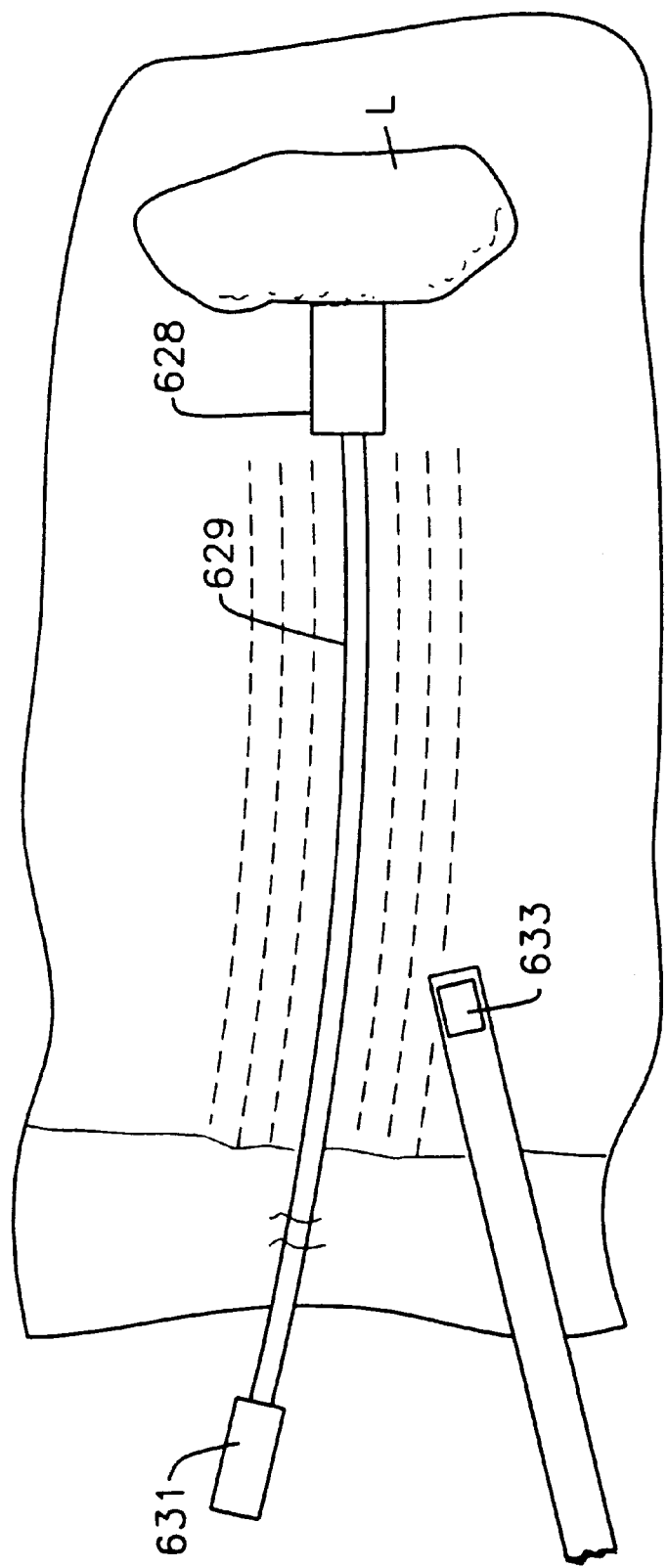

As shown in FIGS. 6 and 7, the display of positions can be provided in multiple planes. Thus, display unit 306 may incorporate a pair of display screens 352 and 356 disposed in perpendicular planes. Each such display unit may display only components of position in directions parallel to the plane of that screen. For example, screen 356 is disposed in a plane perpendicular to the long axis of the patient's body and thus presents an axially directed view showing the representation 206" of the instrument probe tip and the representation 28" of the site probe body in the correct relative positions. Screen 352 is disposed in a plane parallel to the longitudinal axis of the patient's body and presents a saggital view of the relative positions. Other convenient forms of representing three dimensional information can also be employed. For example, the relative positions can be displayed in a stereoscopic imaging device such as a binocular imaging device of the type currently used in "virtual reality" computer graphics applications, in a holographic image or in any other form of three dimensional imaging device. Once the physician has moved the distal tip of the instrument probe to the location of interest, the physician can perform a medical procedure as, for example, a procedure to remove the lesion in its entirety or to perform a biopsy on the lesion. During or after the procedure, site probe body 28 is removed. Where the tissue to which the site probe is anchored is cut from the patient during the procedure, the site probe can simply be pulled out of the patient by means of the control rod 36 (FIG. 1). Alternatively, the anchoring device used in the site probe may permit removal of the site probe from the tissue without removing the tissue. For example, screw 132 (FIG. 2) can be released from the tissue by turning the associated control rod 136. A grapple arrangement may be provided with articulating elements which can be controlled by operation through the control rod, so that the grapple acts as a controllable pincer. In this event, the site probe can be released from the tissue by actuating the grapple to release the tissue.

Computer 304 can calculate the relative positions of the instrument probe distal end 206 and site probe body 28 by subtracting the positions of the two probes. That is, the system may substract the coordinates of the site probe distal end in the external frame of reference defined by external field transducers 300 from the coordinates of the site probe body 28 in the same frame of reference to arrive at the components of the relative position vector from the instrument probe distal end to the site probe body. The relative positions can be provided as a human perceptible indication other than a visual display as, for example, a tactile display or one or more audible signals provided to the physician during navigation of the instrument probe. The calculated relative position can be displayed numerically as well as graphically as, for example, by displaying the individual components of the relative position vector. Also, where the instrument probe is manipulated by automated equipment, the relative position can be provided as vector coordinates or any other convenient form to the automated equipment so as to control the movement of the instrument probe toward the site probe automatically.

As shown in FIG. 8, a reference probe 328 having a reference probe field transducer or position sensor 330 thereon may be used in conjunction with site probe 28. Thus, the reference probe may be positioned in the patient's body adjacent the site probe during the procedure used to place the site probe. The position monitoring system detects the position of the reference probe in the same manner as it detects the positions of the site probe and instrument probe. Any substantial change in the relative positions of the site probe and reference probe indicates that one or the other of these probes has become dislodged from the tissue to which it is anchored. The system may be arranged to issue an automatic warning to the physician, such as a warning tone or visual indication upon occurrence of this condition. Also, the relative disposition of the site probe and reference probe may be recorded during the placement step as, for example, from x-ray or other image data acquired during the placement procedure. This prerecorded disposition data can be compared to the relative disposition of the site probe and the reference probe acquired from the field transducers. Here again, any substantial change in the distance between the site probe and the reference probe indicates that one of the probes has become dislodged.

In the arrangements discussed above, the probes are connected by conductors to the external field transmitting or receiving device. However, such a hard-wired connection is not essential. For example, as shown in FIG. 9, a site probe 428 may include a field transducer in the form of an inductive antenna 430 linked to a capacitor 431 to form a resonant circuit. The external field transducers may apply drive signals in the form of alternating electromagnetic fields to the site probe at the resonant frequency of the circuit in the site probe. The site probe will then radiate electromagnetic fields at the same frequency. Such an arrangement can be used, for example, in a time-multiplex system. During some intervals, the external field transducers are actuated to drive the system. During other intervals the external devices are used as receiving antennas. Alternatively, the reradiating circuit in the site probe may be arranged to receive signals at one frequency and to transmit reradiated signals at a different frequency. As shown in FIG. 9A, a site probe may incorporate a small biocompatible metal pellet 450 with a field transducer in the form of a magnetic metallic element such as 460 disposed therein. In the presence of an externally applied alternating magnetic field, such a pellet will emit a field at the same frequency but out of phase with the external field, thereby altering the phase of the field in the vicinity of the pellet. The degree of phase alteration varies with distance from the pellet over a small region surrounding the pellet. The field transducer of the instrument probe may detect the alternating field, and the phase of the field may be used as an indication of distance from the site probe. Site probes of this nature may be used to mark multiple locations within the body. Such probes can be applied by injection using a syringe and can be fixed in place using a biocompatible adhesive. Site probes which are powered by radiated fields, such as those discussed above with reference to FIGS. 9 and 9A, are particularly useful for long-term implantation. Provided that the site probe remains in place, the instrument probe can be navigated back to the same site even after a long time has elapsed, and even if the site has moved within the body due to growth, healing or other long-term processes. Still other arrangements can use a self-powered site probe, incorporating a storage battery or other source of energy and an internal field generating device such as an oscillator linked to an antenna. Battery-powered site field transducers are particularly useful for applications where the field transducer must be active only for a short time as, for example, where a site probe is used to mark a lesion which will be removed promptly after the field transducer is activated. Alternatively, a battery-powered field transducer may be installed in a long-term application and activated by an externally-applied signal or internal occurrence. More complex forms of such radiating devices can incorporate multiple field transducers or antennas in orthogonal directions for radiating multiple fields. These may be operated at different frequencies or according to a time division multiplexing scheme. Similar arrangements can be used for the instrument probe.

Still other forms of field transducers may be arranged to radiate acoustic fields. Optical radiation, such as visible or infrared light, may also be employed. Many tissues within the body are translucent at red and infrared wavelengths, so that the intensity of optical radiation emitted from a field transducer such as a light emitting diode can be used as an indication of distance from that transducer.

In a system according to yet another embodiment of the invention, the site probe body has a field transducer in the form of a permanent magnet 530 mounted therein. The instrument probe has a field transducer 531 which is adapted to measure constant magnetic field components in a plurality of orthogonal directions in a frame of reference fixed to the distal end 506 of the site probe body. For example, field transducer or position sensor 531 may include a plurality of magnetoresistive, Hall effect or other similar solid state magnetic field transducers, each such transducer being sensitive to a field component in a given local direction relative to the instrument probe 506. The signals from the field transducer 531 represent the components of a vector 533 pointing from the distal end 506 of the instrument probe along the lines of magnetic flux impinging on the distal end. Provided that the distal end 506 is located in a region reasonably close to one of the poles of permanent magnet 530, the vector along the lines of flux points generally in the direction of site probe body 528. The display (not shown) may display this information as a direction vector. The physician must interpret this information as a direction relative to the end of the probe. For example, in using a steerable probe of the type discussed above, the physician can swing the distal end of the probe in various directions and find the direction in which the direction vector points straight ahead from the distal end of the instrument probe. The physician may then advance the instrument probe and repeat the process. In this way, the instrument probe "homes in" on the site probe.

A site probe according to a further embodiment of the invention includes a probe body 628 with an elongated shaft 629. The field transducer in this site probe may be an ultrasonic transducer disposed in the in a handle 631 at the proximal end of shaft 629. Ultrasonic energy supplied by the field transducer is emitted from the site probe along essentially the entire length of the shaft, thus creating a field of ultrasonic energy surrounding the shaft. The field has progressively diminishing intensity in directions away from the shaft. The instrument probe has a field transducer or position sensor 633 in the form of a microphone or other transducer sensitive to ultrasonic energy. The monitoring system is arranged to provide a signal, such as an audible signal having intensity directly related to the intensity of ultrasonic energy impinging on the field transducer or microphone 633. In this way, the system indicates the distance from the tip of the instrument probe to the shaft 629 of the site probe. The physician can use this information to guide the instrument probe into proximity with shaft 629 and to maintain the tip of the instrument probe in proximity with the shaft as the instrument probe is advanced towards the site probe body 629. In a variant of this approach, the ultrasonic energy is emitted only from site probe body 628 itself, so that the ultrasonic field takes the form of a generally spherical field, with the intensity progressively diminishing in all directions away from the probe body. In this case, the sensed intensity represents distance from the site probe body 628. This information can be used to guide the instrument probe as, for example, by moving the instrument probe in various directions and detecting which direction of movement results in the greatest increase in intensity. Similar approaches can be used with magnetic and electromagnetic signals radiated from a site probe. The opposite approach, in which an acoustic or electromagnetic field is radiated from the instrument probe and the intensity of the field impinging on the site probe is monitored, may also be employed. In either approach, the signals from the field transducer or sensor on the probe which acts as the signal receiver indicate the distance between the probes and thus provide information concerning the disposition of the two probes relative to one another.

Figure 12:
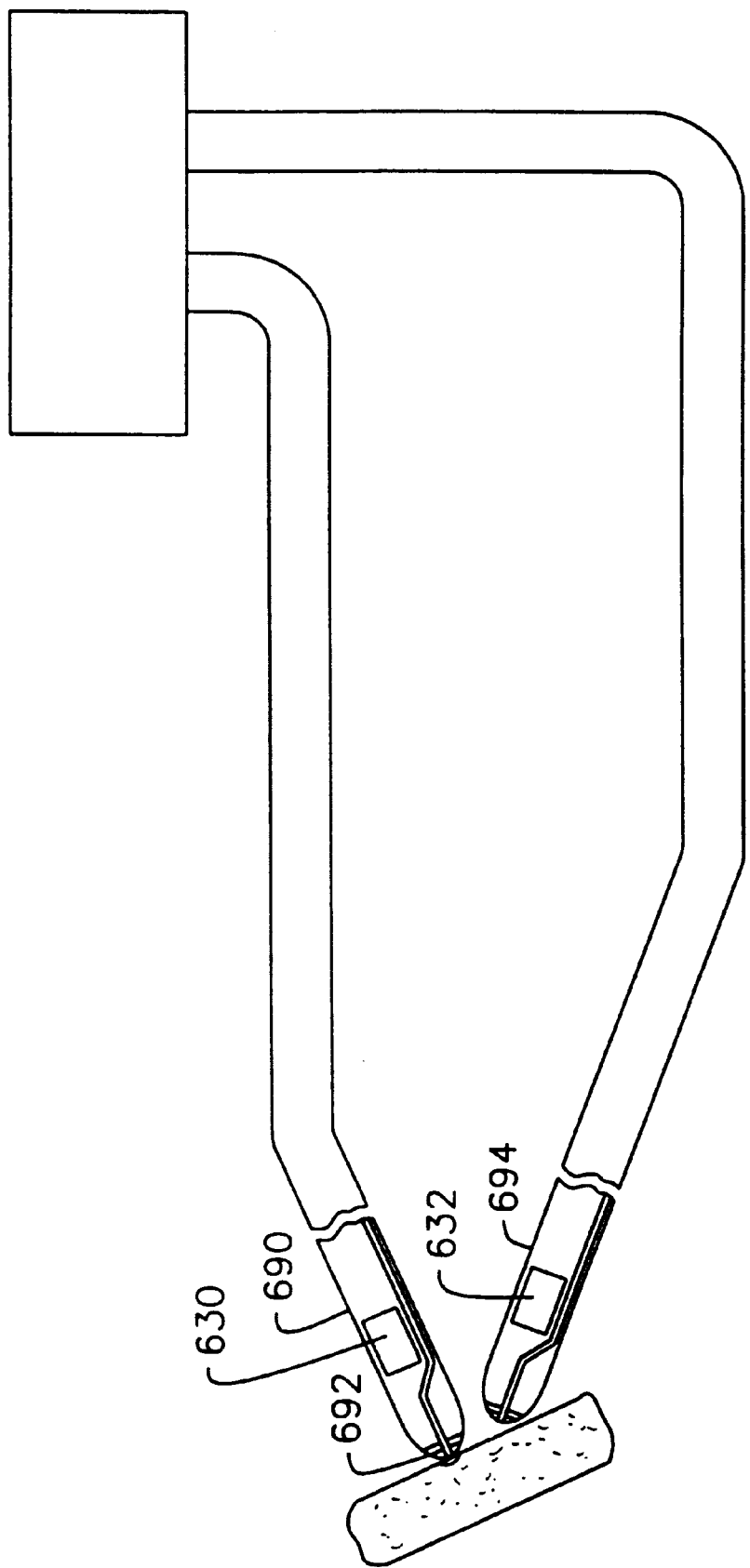

According to further aspects of the invention, information concerning the relative dispositions of a plurality of probes can be used to coordinate the action of the plural probes and to guide one or more of the probes, regardless of whether any of the probes is fixed to the patient's body. For example, in the embodiment depicted in FIG. 12 two instrumented catheters 690 and 694 are coordinated so that their distal ends are juxtaposed with one another. Thus, positional information derived by position sensors 630 and 632 adjacent the distal tips of catheter 690 and 694 is used by the physician to navigate both catheters into position adjacent a common treatment location 692. Moreover, the position sensors 630 and 632 provide information concerning the orientations of both catheters relative to one another and relative to the common treatment location 692, so that the tips of both catheters can be aimed onto the common treatment location. The disposition-determining systems discussed above with reference to the instrument probes and site probes can be used to provide information concerning the relative dispositions of multiple probes either by measuring the disposition of each probe in an external frame of reference or by monitoring fields transmitted between field transducers on the multiple probes and determining relative dispositions directly from such monitored fields. It is useful to coordinate the actions of multiple catheters in catheter-based surgical procedures as, for example, where multiple different tools must be brought to a common location so that the common location can be treated by all of the tools. Also, one or more of the catheters may carry devices for observing the treatment as, for example, optical or ultrasonic viewing equipment, whereas the other catheters may carry devices for manipulating, cutting or excavating tissues. The tissues can be cut or "excavated" by action of a laser beam directed out of a catheter tip or, alternatively, by applying small gas bubbles ("microbubbles") and causing rupture of the same by applying ultrasonic energy to the area infused with microbubbles. Coordinated catheters can be used in such surgical operations as, for example, by applying the laser light or microbubbles through one catheter and observing the process through another catheter.

Figure 13:
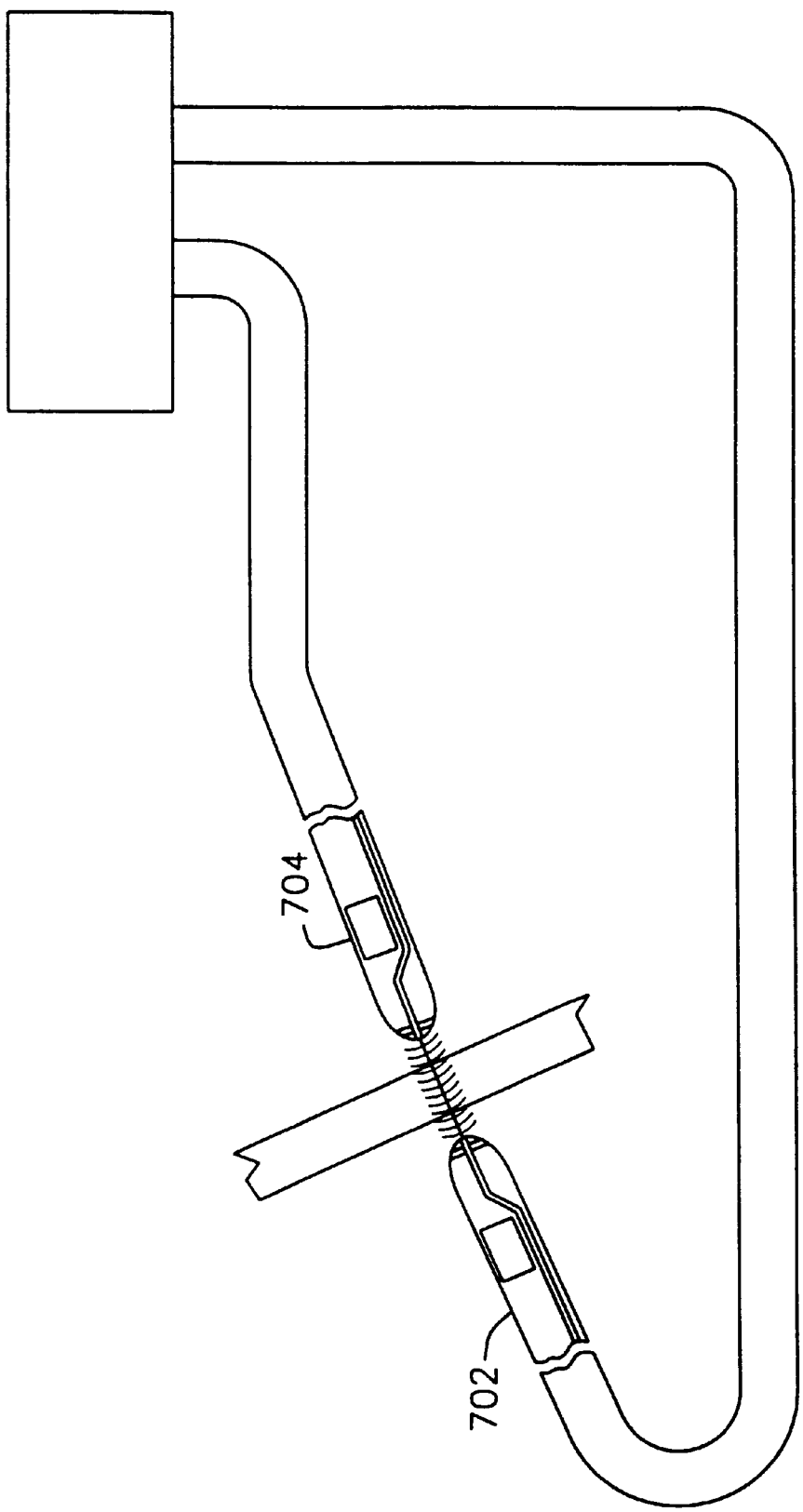

As shown in FIG. 13, plural probes can be coordinated with one another using information concerning their relative dispositions even without bringing the probes into close proximity to one another. Thus, in the embodiment of FIG. 13, probes 702 and 704 lie on opposite sides of a bodily structure, but are aligned and aimed towards one another using positional information derived from position sensors or field transducers carried on the probes. Probes pointing towards one another can be used for a variety of purposes. For example, probe 702 may transmit ultrasound to a detector on probe 704 and a detector on probe 704 may be actuated to generate an ultrasonic image of the tissues between the probes. Alternatively, probes which are initially disposed at a distance from one another can be aligned with one another and then one or both of the probes can be advanced towards the other probe, so that the probes are brought together in much the same manner as the site probe and instrument probe discussed above. In this arrangement, however, neither probe is fixed to the body tissue during the procedure.

Figure 14:
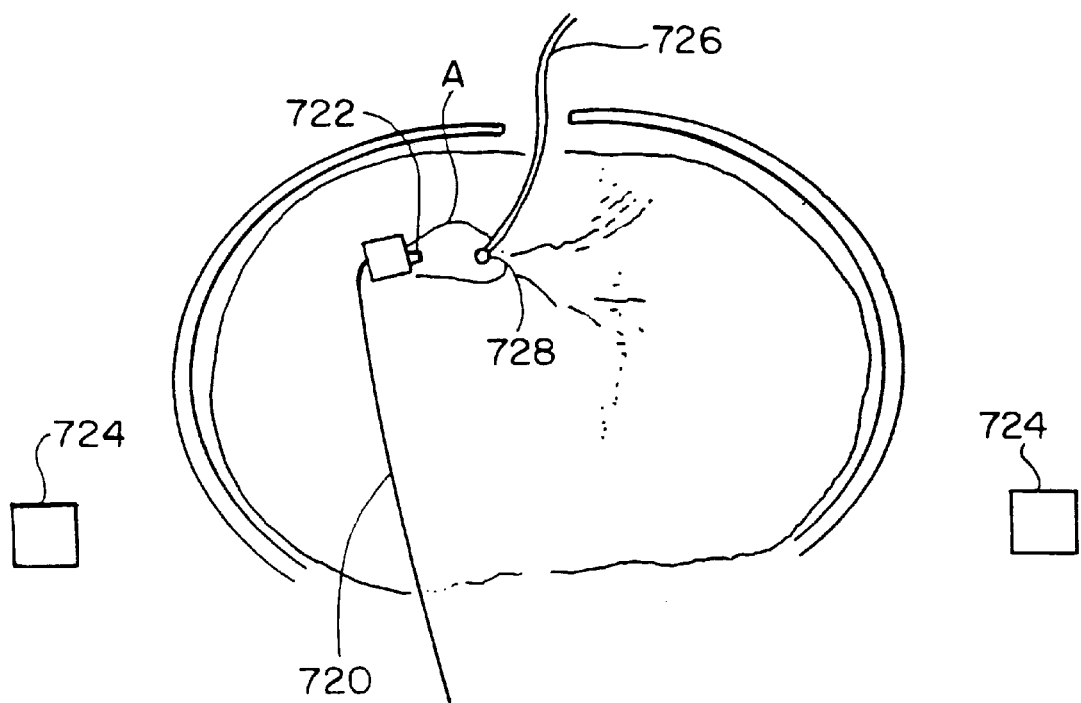

In procedures according to further embodiments of the invention, two or more probes can be coordinated by engaging both probes with related body structures or with spaced-apart locations in a body structure. For example, where a first probe is disposed within an intrabody lumen such as a vascular structure, the second probe may be disposed in another part of the same lumen. In a procedure according to a further embodiment of the invention using this approach, (FIG. 14), a first probe in the form of a catheter 720 may be threaded through the vascular system and positioned in an artery within the brain upstream from an aneurysm in the brain. Catheter 720 may incorporate a first field transducer or position sensor 722 adjacent its distal end. The step of positioning catheter 720 may be conducted using conventional imaging techniques such as fluoroscopic guidance. Alternatively or additionally, the techniques disclosed in the '091 Patent may be used. Thus, the disposition of field transducer 722 may be detected by means of fields transmitted to or from one or more additional field transducers, the detected disposition is correlated to the frame of reference of previously-acquired imaging data, and a representation of the catheter tip is superposed on a display showing the image from the previously-acquired data. After catheter 720 is placed, a first medical procedure is performed by inflating a balloon 726 adjacent the distal end of the catheter so as to block the blood supply to the artery at a first location upstream from the aneurysm A. A second probe in the form of a second catheter 726 having a field transducer 728 adjacent its distal end is advanced into the same artery through the surrounding brain tissue from outside of the artery at a second location downstream from the first location. The second probe is then used to place a stent or perform other treatment at the second location. During placement of the second probe, information concerning the relative disposition of the first and second probes can be used to position the second probe at the desired location with respect to the first probe, and thereby position the second probe at the desired location with respect to the artery and aneurysm.

The relative disposition information can be used in conjunction with other sources of disposition information. For example, information concerning the disposition of second probe distal end or field transducer 728 relative to first probe distal end or field transducer 722 can be used in conjunction with a superposition scheme as described in the '091 patent, in which a representation of the second probe distal end is displayed in registration with a previously-acquired image. The superposition scheme can be used to guide the second probe around structures such as critical areas of the brain far from the first probe, whereas the relative position information can be used to bring the second probe to a precise placement. The relative disposition information can be combined with direct image guidance in similar manner. Use of relative disposition information in conjunction with other information can be adapted to procedures in other regions of the body.

Figure 15:
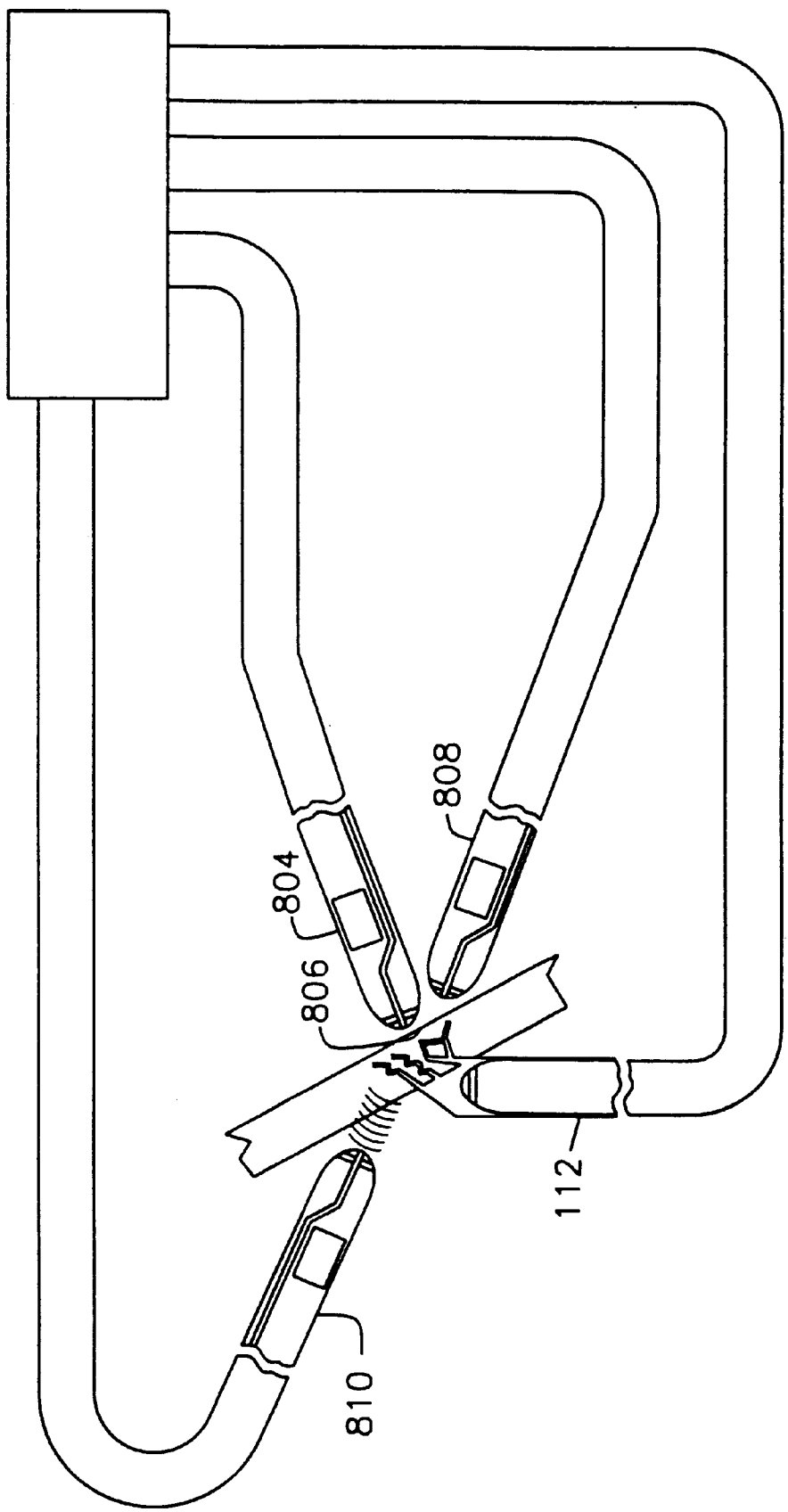
Figure 16:
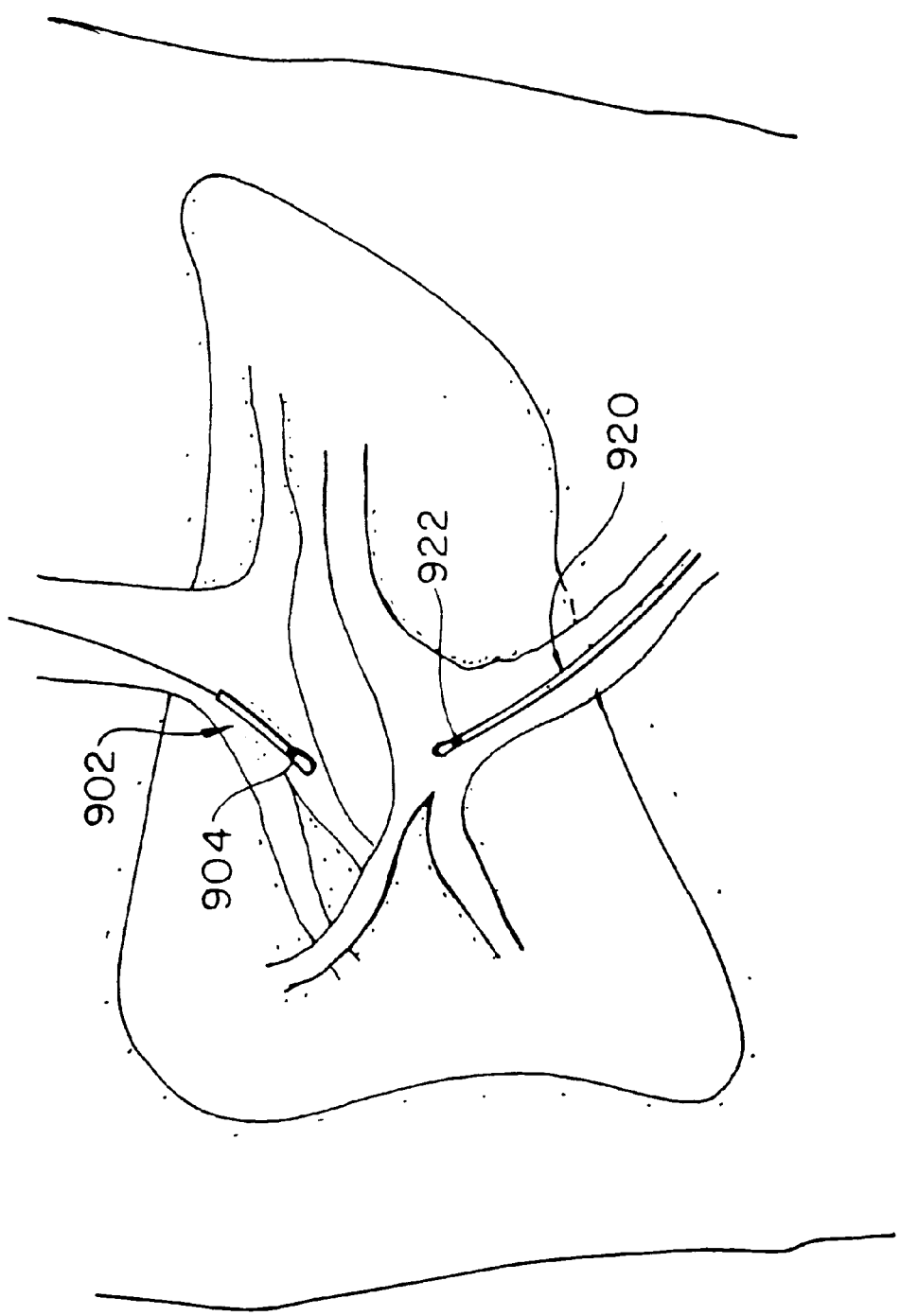

Other procedures wherein plural probes are placed on separated but functionally related sites include placement of two probes on separate points along a nerve for stimulation and measurement of nerve impulse travel, and placement of an infusion catheter along a blood vessel and a sampling catheter in the vascular bed served by that blood vessel. As depicted in FIG. 15, more than two probes can be coordinated in a similar fashion. Thus, in the four-catheter arrangement of FIG. 15, catheter 804 is excavating tissue at a location 806, whereas catheter 808 is removing the debris from such location. Catheter 810 is viewing the tissue surrounding location 806 using an ultrasonic imaging system carried on the catheter, whereas catheter 112 is injecting microbubbles into the vascular bed at location 106 to enhance the contrast between various types of tissues at such location.

The use of multiple probes is advantageous in that each probe need only accommodate one or a few devices. The individual probes may be simpler and smaller in size than a composite probe incorporating all of the required devices. The preferred field transducers and probes utilized in accordance with the present invention desirably are small-diameter devices to facilitate insertion into the body. Thus, each field transducers desirably has a smallest dimension less than about 3 mm, preferably less than 2 mm, more preferably less than about 1 mm; still more preferably less than about 0.2 mm and most preferably even smaller. The probe itself desirably has dimensions, at the field transducer, in the same ranges. Among the field transducers which can be employed are those disclosed in copending, commonly assigned United States Provisional Patent Application 012, 242 Filed Feb. 26, 1996 and in the PCT International Application entitled Catheter With Lumen, naming Biosense, Inc. as an applicant, filed of even date herewith in the United States Receiving Office and claiming priority of said '242 application, the disclosures of which are hereby incorporated by reference herein.

One medical procedure which can be performed using the techniques discussed above is a liver bypass. Patients who have advanced chirosis of the liver suffer, as a result of blockage of the portal vein, from elevated venous blood pressure, which may cause fatal GI bleeding. In the bypass procedure, a shunt is created between the hepatic vein and the portal vein in the liver to bypass most of the liver. Thus, the venous blood pressure is reduced and GI bleeding eliminated. As disclosed, for example, by Zemel et al., Technical Advances in Transjugular Intrahepatic Portosystemic Shunts, RadioGraphics, Vol. 12, No. 4, pp. 615–623 (1992), the disclosure of which is incorporated by reference herein, a catheter and guidewire are inserted through the jugular vein into the hepatic vein, and a needle is passed along the guidewire and used to probe for the portal vein. The needle is forcibly advanced through the liver tissue towards the portal vein. This entails considerable difficulty if the liver tissue is toughened or scarred as occurs in some diseases. Since the needle is hollow, when the other portal is found, blood flows through the needle. A catheter may replace the needle, so that the catheter extends between the veins. A stent such as an inflatable stent is guided along the needle or catheter to form a permanent passageway connecting the two veins. The opposite procedure, wherein entry is made from the portal vein and the needle is passed through the liver tissue to the hepatic vein, can also be employed. This procedure is performed using a fluoroscope and is very lengthy, so the amount of radiation exposure of the patient and the surgeon is considerable.

According to further aspects of the present invention, such a procedure can be greatly facilitated by using non-ionizing radiation transmitted to field transducer on a needle or other probe used to form the passageway, and determining the disposition of the probe during the procedure using such non-ionizing radiation. As shown in FIG. 15, a needle 902 with a field transducer or position sensor 904 thereon is introduced into the hepatic vein. A site probe 920 having a position sensor or field transducer 922 thereon is disposed in the liver parenchyma adjacent to the portal vein. The needle is guided toward the portal vein by monitoring the relative dispositions of the needle and marker catheter in the manner discussed above while the needle is advanced through the liver tissue. One the needle has penetrated to the portal vein, the remainder of the procedure is performed in the conventional manner. In a further embodiment of the invention, the position of a needle with a position sensor thereon is monitored and the position information is registered with a previously-acquired image of the patient such as a CT image made using an intravenous contrast medium. As described in the aforementioned U.S. Pat. No. 5,558,091, such registration can be achieved by means of fiducial markers imaged along with the patient. As the needle is advanced through the liver tissue, a representation of the needle tip is superposed on the displayed image, thereby allowing the physician to guide the needle from the hepatic vein toward the portal vein or vice-versa. In any of the above-described procedures for tunneling through the liver tissue, passage of the needle can be facilitated by destroying the intervening tissue using a laser or by instilling microbubbles into the tissue ahead of the needle and applying focused ultrasound to destroy the tissue. Where these techniques are employed, the needle may be replaced by a flexible device such as a catheter.

Figure 17:
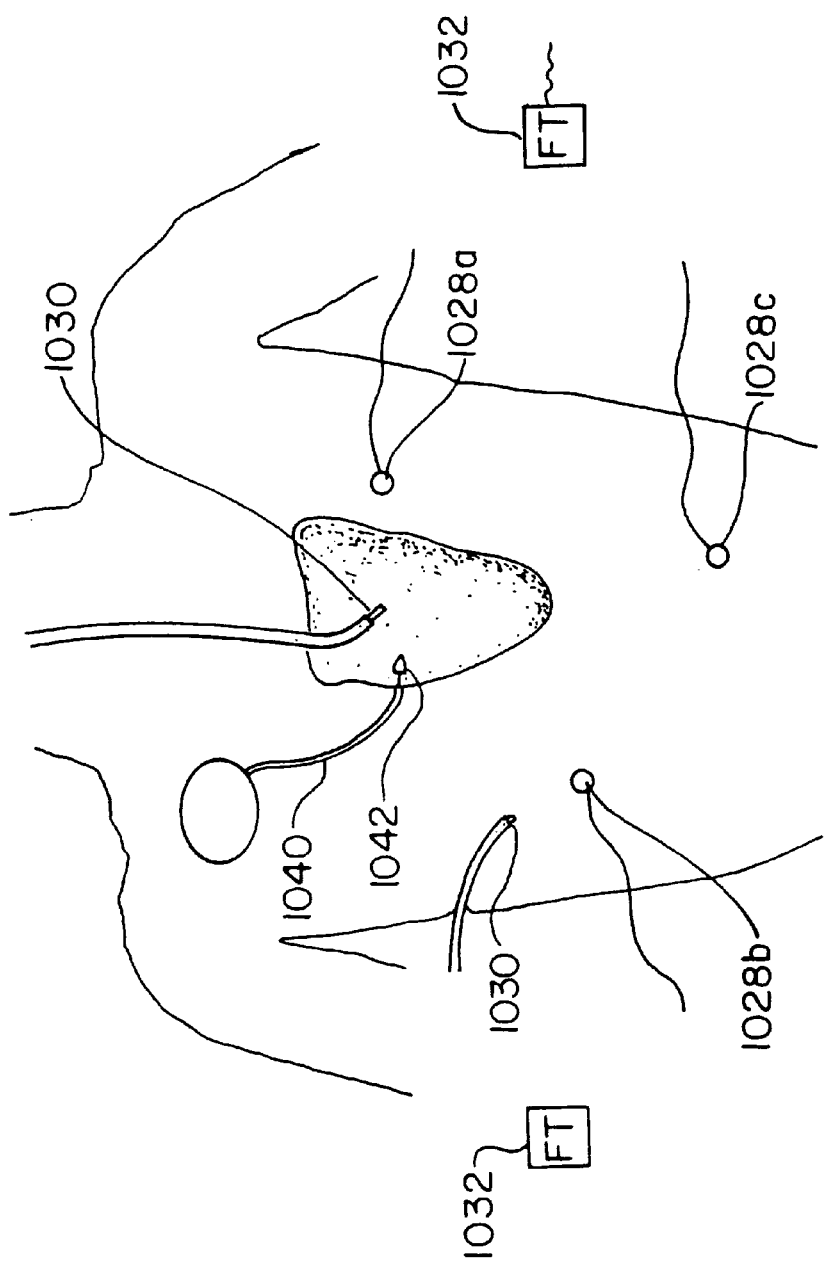

As shown in FIG. 17, numerous site probes 1028a–1028c with field transducers thereon can be disposed at distant locations within the body of the patient to guide one or more instrument probes, also equipped with field transducers, 1030 to any of these locations. The numerous probes can also be employed in conjunction with additional field transducers disposed outside of the body, such as reference field transducers 1032 disposed in a fixed frame of reference. In one arrangement, reference field transducers 1032 act as signal transmitters, whereas the field transducers on all probes 1028 and 1030 act as receivers. In other arrangements, the field transducers act as transmitters. Various multiplexing and signal separation arrangements can be used to avoid interference between the field transducers associated with the multiple probes. For example, field transducers associated with each of the site probes 1028 may be low-powered transmitting devices such as the re-radiating devices discussed above with reference to FIGS. 9 and 9A, and the field transducer of the instrument probes 1030 may be relatively insensitive receivers, or vice-versa, so that each instrument probe will interact with the closest site probe but will not interact with other site probes. Frequency-division multiplexing, code diversity multiplexing and time division multiplexing, as well as combinations of these multiplexing schemes may be employed. For example, the various reference field transducers 1032 may transmit at different frequencies, whereas each of the field transducers 1028a, 1028b and 1028c of the site probes may transmit at other frequencies, these frequencies being different from one another. Alternatively or additionally, the various field transducers used in a single procedure may use different types of fields. Thus, the field transducers associated with some of the probes may be transmit or receive optical or acoustic fields, whereas others may transmit or receive magnetic or electromagnetic fields. In the embodiment of FIG. 17, and in the other embodiments discussed above, the same field transducer of the instrument probe 1030 may be used both to establish disposition relative to site probes 1028 and to establish position in the frame of reference of reference transducers 1032 as, for example, for use in displaying position of the instrument probe superposed on an image of the patient.

As also illustrated in FIG. 17, cardiac pacemaker lead 1040 is provided with a field transducer 1042 adjacent the distal tip of the lead. The cardiac pacemaker lead is implanted for long-term use in the conventional manner. Desirably, transducer 1042 is arranged so that it can operate without a lead-supplied power source. For example, transducer 1042 may be a permanent magnet or reradiating field transducer as discussed above. Thus, even if lead 1040 breaks, an instrument probe may be brought into proximity with the distal end and used to remove the distal end. The same techniques can be used to mark other implanted devices such as orthopedic implants, and tools which are not deliberately implanted but which may be accidentally lost during surgery.

Figure 5:
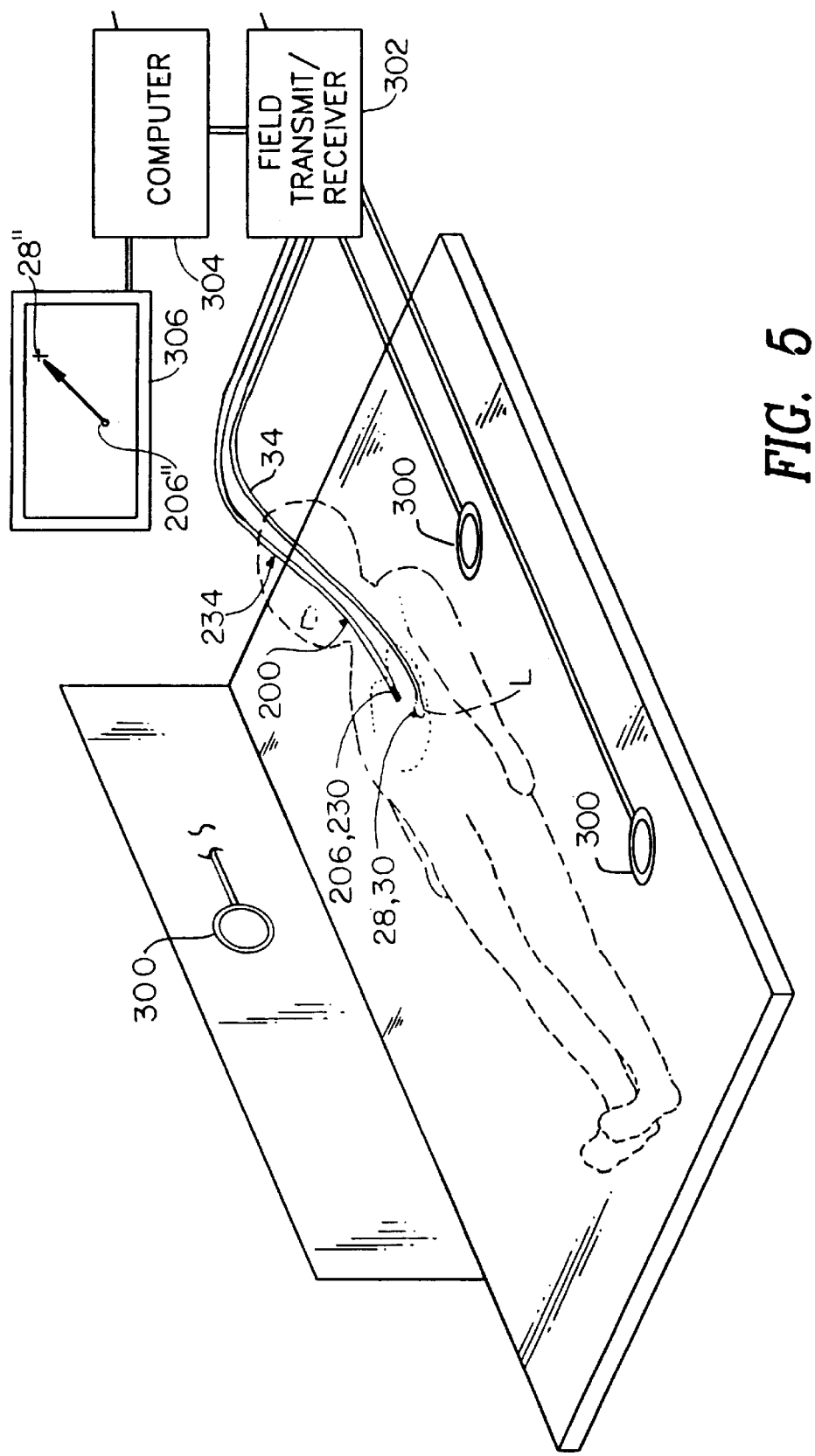
FIG. 5 is a diagrammatic perspective view depicting a patient and apparatus during performance of a process in accordance with one embodiment of the invention.
Figure 18:
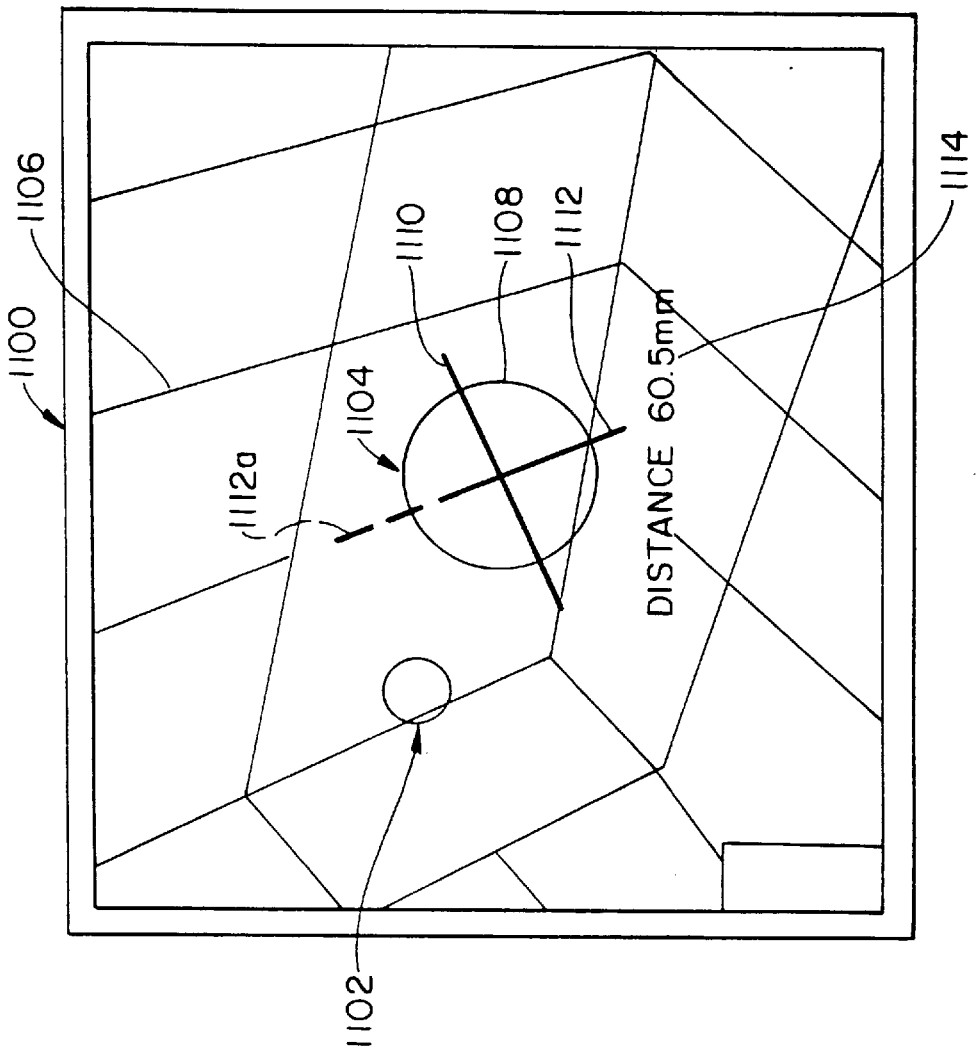
FIG. 18 is a an elevational view depicting a computer screen display utilized in certain embodiments of the invention.

A preferred screen display for indicating the relative dispositions of probes is depicted in FIG. 18. This may be used in place of the arrow 306 discussed above with reference to FIG. 5. A display device such as a computer screen 1100 shows a representation 1102 of a site probe disposed within the patient and a representation 1104 of an instrument probe being guided toward the patient. Optionally, both of these representations are displayed against a background of grid lines 1106 representing Cartesian (x-y-z) coordinates of a reference coordinate system such as the coordinate system of the external field transducers. Thus, the site probe representation 1102 may be in the form of a sphere or other arbitrary shape. Instrument probe representation 1104 includes a sighting aperture 1108 in the form of a circle or other closed or semi-closed geometric figure, as well as crossing lines 1110 and 1112 representing directions perpendicular to the a preselected axis of the instrument probe, preferably the long axis of the probe at the tip of the probe. The directions of lines 1110 and 1112 may correspond to the pitch and yaw axes 239 and 241 (FIG. 4) of the instrument probe. These directions are fixed with respect to the instrument probe distal tip, so that when the instrument probe rolls around its long axis, the directions of lines 1110 and 1112 move in the same manner. One end 1112a of line 1112 has a different appearance from the other lines so that the user can track the roll orientation of the instrument probe tip visually. Pitch and yaw movements of the instrument probe distal tip, around axes 239 and 241, (FIG. 4) are shown by movement of the coordinate system and site probe representation relative to the screen and relative to the instrument probe representation 1104. Thus, the view of grid lines 1106 representing the coordinate system, as well as the view of site probe representation 1102 which is displayed on the screen is a projection in a plane perpendicular to the long axis of the instrument probe at the tip of the probe. By moving and/or bending the instrument probe so that the site probe representation is aligned with the instrument probe representation, as by centering sphere 1102 in circle 1108 of instrument probe representation 1104, the physician can point the instrument probe long axis or roll axis 237 (FIG. 4) directly at the site probe. Advancement of the instrument probe in this condition will bring the instrument probe directly towards the site probe. The physician can use the displayed information to navigate the instrument probe to one side of the site probe.

Distance between the tip of the instrument probe and the site probe is represented by the size of the site probe representation 1102 relative to the instrument probe representation 1104. Preferably, the instrument probe representation has a fixed size, whereas the site probe representation grows as the distance decreases and shrinks as the distance decreases. In a particularly preferred arrangement, the site probe representation completely fills circle 1108 when the tip is at the site probe. Other representations of distance, such as alphanumeric display 1114 and bar graph 1116 are also provided. As these and other variations and combinations of the features described above can be utilized without departing from the present invention, the foregoing description of the preferred embodiments should be taken by way of illustration rather than by way of limitation of the invention as defined by the claims.

INDUSTRIAL APPLICABILITY

The invention can be used in medical and related procedures.

What is claimed is:

1. A method of guiding a probe in the body of a patient comprising the steps of:
   (a) providing a site probe at a site within the body of a patient and providing a instrument probe to be guided within the body of the patient;
   (b) transmitting one or more non-ionizing fields to or from each of said probes and detecting each such transmitted field; and
   (c) determining the relative disposition of said instrument probe and said site probe by determining a position of each said probe in a common frame of reference based upon the properties of said detected fields and determining said relative disposition based upon the so-determined positions; and
   (d) directing said instrument probe toward said site probe based on relative deposition.

2. A method as claimed in claim 1 wherein said directing step includes the step of pointing said instrument probe toward said site probe.

3. A method as claimed in 1 wherein said directing step includes the step of moving said instrument probe toward said site probe.

4. A method as claimed in claim 3 wherein said transmitting step includes the step of generating magnetic fields at said external elements and said detecting step includes the step of detecting said magnetic fields at said probes.

5. A method as claimed in claim 3 wherein said determining step includes the steps of calculating the position of each said probe in said frame of reference and calculating a distance and direction between said instrument and said site from said positions.

6. A method as claimed in claim 1 further comprising the step of providing one or more elements external to the body of the patient defining said frame of reference, said step of transmitting said fields to or from said probes including the step of transmitting said fields between said probes and said external elements so that at least one property of each such detected field depends upon the dispositions of said probes relative to said one or more external elements.

7. A method as claimed in claim 1 further comprising the steps of placing a reference probe in or on the body of the patient, said transmitting and detecting steps including the steps of transmitting one or more fields to or from said reference probe, and detecting such fields so that at least one property of the detected fields depends upon a disposition of said reference probe, the method further comprising the step of determining a relative disposition of said reference probe and said site probe based upon one or more properties of detected fields.

8. A method as claimed in claim 7 wherein said steps of placing said site probe and said reference probe include the step of placing said reference probe adjacent said site probe.

9. A method as claimed in claim 8 wherein both said site probe and said reference probe are placed on or adjacent to a lesion.

10. A method as claimed in claim 7 further comprising the step of providing a warning signal in response to a change in said spatial relationship between said site probe and said reference probe.

11. A method as claimed in claim 7 further comprising the step of determining a relative disposition of said site probe and said reference probe by imaging the patient and providing a warning signal if the spatial relationship determined based upon said detected fields is different than the spatial relationship determined in said imaging step.

12. A method of guiding a probe in a medical patient comprising the steps of:
    (a) providing a site probe at a site within the body of a patient and providing a instrument probe to be guided within the body of the patient;
    (b) transmitting one or more magnetic fields to or from each of said probes and detecting each such transmitted field;
    (c) determining the relative disposition of said site probe and said instrument probe from the properties of said detected fields;
    (d) providing an indication of said relative disposition; and
    (e) moving said instrument probe within the body of the patient toward said site in response to said indication.

13. A method as claimed in claim 12 wherein said step of providing an indication includes the step of providing said indication in human-perceptible form and said moving step includes the step of manually controlling movement of the instrument probe within the body in response to said indication.

14. A method as claimed in claim 12 wherein said step of providing said indication includes the step of providing said indication in the form of one or more audible signals.

15. A method as claimed in claim 12 wherein said moving step includes the step of automatically controlling movement of the instrument within the body in response to said indication.

16. A method as claimed in claim 12 wherein said step of providing said probes includes the step of imaging the patient's body and placing said site probe at said site using the data in said image.

17. A method as claimed in claim 16 wherein said placing step is conducted during the imaging step and said imaging step is performed so that said site probe is included in said image.

18. A method as claimed in claim 17 wherein said site is a site adjacent a lesion, said imaging step being performed so that said lesion is included in the image, the method further including the step of treating the lesion using said instrument probe after said moving step, whereby the instrument is guided to the lesion during said moving step.

19. A method as claimed in claim 13 wherein said step of determining relative disposition includes the step of determining distance between said instrument and said site.

20. A method as claimed in claim 19 wherein said step of determining relative disposition includes the step of determining only said distance, without determining direction from said instrument to said site.

21. A method as claimed in claim 20 wherein said step of determining relative disposition includes the step of determining direction from said instrument to said site.

22. A method as claimed in claim 12 wherein said transmitting, detecting and determining steps and said step of providing said perceptible indication are performed during said moving step so as to alter said perceptible indication in real time as the instrument moves.

23. A method of coordinating two probes, comprising:
    (a) providing a first and second probe, each of which has a field transducer mounted thereon;

(b) performing a first medical procedure at a first location using the first probe;

(c) performing a second medical procedure at a second location using the second probe;

(d) determining the relative positions of the probes in a common frame of reference by transmitting one or more non-ionizing magnetic fields to or from said field transducers on said probes; and (e) coordinating the two medical procedures using the determined relative positions in the common frame of reference.

24. A method according to claim 23, wherein the second probe is a microbubble injecting probe.

25. A method according to claim 23, wherein said step of determining the relative positions of the probes comprises:

(a) determining the position of the first probe using non-ionizing magnetic radiation;

(b) determining the position of the second probe using non-ionizing magnetic radiation; and (c) subtracting the two positions.

26. A method of displaying the relative positions of an instrument and a site within the body of a living subject for directing the instrument toward the site comprising the steps of:

(a) providing an arbitrary representation of the instrument on a planar display;

(b) providing a projection of space in a plane perpendicular to an axis of the instrument on said display, said projection of space including an arbitrary representation of the site, said projection being selected so that said representation of said site is aligned with said representation of the instrument when said axis of said instrument is aligned with said site; and (c) altering the relative sizes of said site representation relative to said instrument representation as distance between said instrument and said site change.

27. A method as claimed in claim 26 wherein said altering step is conducted so that the size of the site representation increases as said distance decreases.

28. A method as claimed in claim 26 wherein said projection of space includes representations of a fixed coordinate system, whereby said fixed coordinate representations will move on said display as orientation of said axis of said instrument changes.

29. A method of coordinating a plurality of probes, comprising:

(a) providing a first probe, a second probe, and a third probe each of which has a field transducer mounted thereon;

(b) performing a first medical procedure at a first location using the first probe;

(c) performing a second medical procedure at a second location using the second probe;

(d) performing a third medical procedure at a third location using the third probe, wherein the third medical procedure is coordinated with the two medical procedures;

(e) determining the relative positions of the probes by transmitting one or more nonionizing fields to or from said field transducers on said probes; and (f) coordinating the medical procedures using the determined relative positions.

30. A method of coordinating two probes, comprising;

(a) providing a first and second probe, each of which has a field transducer mounted thereon, wherein the second probe is an ultrasonic imaging probe;

(b) performing a first medical procedure at a first location using the first probe;

(c) performing a second medical procedure at a second location using the second probe;

(d) determining the relative positions of the probes by transmitting one or more non-ionizing fields to or from said field transducers on said probes; and (e) coordinating the two medical procedures using the determined relative positions.

31. A method of coordinating two probes, comprising:

(a) providing a first and second probe, each of which has a field transducer mounted thereon;

(b) performing a first medical procedure at a first location using the first probe;

(c) performing a second medical procedure at a second location using the second probe;

(d) determining the relative positions of the probes by transmitting one or more non-ionizing fields to or from said field transducers on said probes; and (e) coordinating the two medical procedures using the determined relative positions wherein the medical procedure performed using said first probe forms debris and said second probe is a vacuuming probe which removes said debris.

* * * * *